(12) United States Patent  
Douk et al.

(10) Patent No.: US 7,972,370 B2
(45) Date of Patent: Jul. 5, 2011

(54) STENT GRAFT SYSTEM AND METHOD OF USE

(75) Inventors: Nareak Douk, Lowell, MA (US); Nasser Rafiee, Andover, MA (US); Morgan House, Newfields, NH (US); Jia Hua Xiao, Santa Rosa, CA (US); Walter Bruszewski, Guerneville, CA (US); Peggy Grills, Hidden Valley Lake, CA (US); James Machek, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 324 days.

(21) Appl. No.: 12/109,186

(22) Filed: Apr. 24, 2008

(65) Prior Publication Data

US 2009/0270966 A1 Oct. 29, 2009

(51) Int. Cl.
*A61F 2/06* (2006.01)
(52) U.S. Cl. .................................. 623/1.13; 623/1.36
(58) Field of Classification Search .................. 606/139, 606/144, 148, 150; 623/1.11, 1.13, 1.14, 623/1.36
See application file for complete search history.

(56) References Cited

U.S. PATENT DOCUMENTS

| | | | |
|---|---|---|---|
| 4,333,469 A * | 6/1982 | Jeffcoat et al. ................ 607/5 |
| 4,427,964 A * | 1/1984 | Ruegsegger ................ 337/231 |
| 5,545,148 A | 8/1996 | Wurster | |
| 5,582,616 A | 12/1996 | Bolduc et al. | |
| 5,669,919 A | 9/1997 | Sanders et al. | |
| 5,682,906 A | 11/1997 | Sterman et al. | |
| 5,810,882 A | 9/1998 | Bolduc et al. | |
| 5,891,159 A | 4/1999 | Sherman et al. | |
| 5,935,138 A | 8/1999 | McJames, II et al. | |
| 5,972,020 A | 10/1999 | Carpentier et al. | |
| 6,159,240 A | 12/2000 | Sparer et al. | |
| 6,182,664 B1 | 2/2001 | Cosgrove | |
| 6,250,308 B1 | 6/2001 | Cox | |
| 6,258,069 B1 | 7/2001 | Carpentier et al. | |
| 6,511,506 B2 * | 1/2003 | Chevillon et al. ............ 623/1.36 |
| 6,514,263 B1 | 2/2003 | Stefanchik et al. | |
| 6,524,338 B1 | 2/2003 | Gundry | |
| 6,562,051 B1 | 5/2003 | Bolduc et al. | |
| 6,619,291 B2 | 9/2003 | Hlavka et al. | |
| 6,626,917 B1 | 9/2003 | Craig | |
| 6,663,633 B1 | 12/2003 | Pierson, III | |
| 6,689,164 B1 | 2/2004 | Seguin | |
| 6,702,826 B2 | 3/2004 | Liddicoat et al. | |
| 6,800,081 B2 * | 10/2004 | Parodi .......................... 606/139 |
| 6,840,246 B2 | 1/2005 | Downing | |
| 6,884,248 B2 | 4/2005 | Bolduc et al. | |
| 6,902,570 B2 | 6/2005 | Schraft et al. | |

(Continued)

FOREIGN PATENT DOCUMENTS

WO WO01/00114 1/2001

(Continued)

*Primary Examiner* — Anhtuan Nguyen
*Assistant Examiner* — Jonathan W Miles

(57) ABSTRACT

A stent graft system and method of use includes a stent graft for fixation at an attachment site with graft material defining at least one opening having an opening perimeter; a support attached to the graft material; a guide rail attached around the opening perimeter; and a helical anchor having a plurality of coils with a point at one end. The plurality of coils are rotatable around the guide rail to cause the pointed end of the coils to penetrate the graft material and the adjacent tissue in contact with the stent graft to sew the stent graft to the attachment site.

9 Claims, 22 Drawing Sheets

U.S. PATENT DOCUMENTS

| | | |
|---|---|---|
| 7,118,595 B2 | 10/2006 | Ryan et al. |
| 7,175,659 B2 | 2/2007 | Hill et al. |
| 2002/0156526 A1 | 10/2002 | Hlavka et al. |
| 2002/0161378 A1 | 10/2002 | Downing |
| 2003/0176917 A1 | 9/2003 | Ryan et al. |
| 2003/0220685 A1 | 11/2003 | Hlavka et al. |
| 2004/0024414 A1 | 2/2004 | Downing |
| 2004/0153147 A1 | 8/2004 | Mathis |
| 2004/0236419 A1 | 11/2004 | Milo |
| 2005/0027352 A1 | 2/2005 | Cosgrove et al. |
| 2005/0049698 A1 | 3/2005 | Bolling et al. |
| 2005/0065601 A1 | 3/2005 | Lee et al. |
| 2005/0075659 A1 | 4/2005 | Realyvasquez et al. |
| 2005/0131533 A1 | 6/2005 | Alfieri et al. |
| 2005/0171601 A1 | 8/2005 | Cosgrove et al. |
| 2005/0177180 A1 | 8/2005 | Kaganov et al. |
| 2007/0027533 A1 | 2/2007 | Douk |
| 2007/0051377 A1 | 3/2007 | Douk et al. |
| 2007/0083259 A1 | 4/2007 | Bloom et al. |

FOREIGN PATENT DOCUMENTS

| | | |
|---|---|---|
| WO | WO02/062263 | 8/2002 |
| WO | WO03/105667 | 12/2003 |
| WO | WO2004/045463 | 6/2004 |
| WO | WO2004/112585 | 12/2004 |
| WO | WO2005/025644 | 3/2005 |
| WO | WO2005/046488 | 5/2005 |
| WO | WO2005/058206 | 6/2005 |

\* cited by examiner

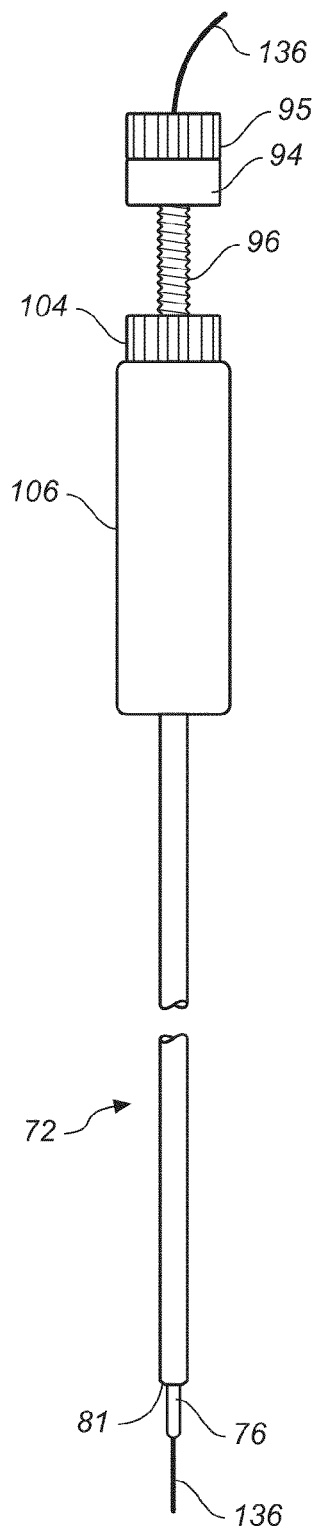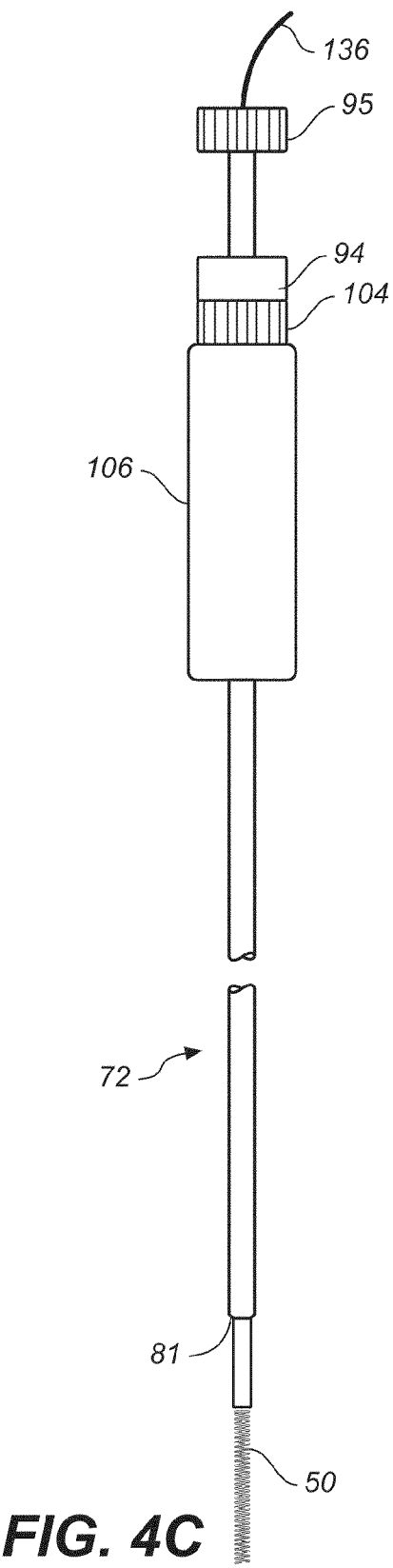
*FIG. 4B*  *FIG. 4C*

STENT GRAFT SYSTEM AND METHOD OF USE

TECHNICAL FIELD

The technical field of this disclosure is medical implantation devices, particularly, a stent graft system and method of use.

BACKGROUND OF THE INVENTION

Wide ranges of medical treatments have been developed using endoluminal prostheses, which are medical devices adapted for temporary or permanent implantation within a body lumen, such as naturally occurring or artificially made lumens. Examples of lumens in which endoluminal prostheses may be implanted include arteries such as those located within coronary, mesentery, peripheral, or cerebral vasculature; arteries; gastrointestinal tract; biliary tract; urethra; trachea; hepatic shunts; and fallopian tubes. Various types of endoluminal prostheses have also been developed with particular structures to modify the mechanics of the targeted lumen wall.

A number of vascular devices have been developed for replacing, supplementing, or excluding portions of blood vessels. These vascular devices include endoluminal vascular prostheses and stent grafts. Aneurysm exclusion devices, such as abdominal aortic aneurysm (AAA) devices, are used to exclude vascular aneurysms and provide a prosthetic lumen for the flow of blood. Vascular aneurysms are the result of abnormal dilation of a blood vessel, usually from disease or a genetic predisposition, which can weaken the arterial wall and allow it to expand. Aneurysms can occur in any blood vessel, but most occur in the aorta and peripheral arteries, with the majority of aneurysms occurring in the abdominal aorta. An abdominal aneurysm typically begins below the renal arteries and extends into one or both of the iliac arteries.

Aneurysms, especially abdominal aortic aneurysms, have been commonly treated in open surgery procedures where the diseased vessel segment is bypassed and repaired with an artificial vascular graft. While open surgery is an effective surgical technique in light of the risk of a fatal abdominal aortic aneurysm rupture, the open surgical technique suffers from a number of disadvantages. It is complex, requires a long hospital stay, requires a long recovery time, and has a high mortality rate. Less invasive devices and techniques have been developed to avoid these disadvantages. Tubular endoluminal prostheses that provide a lumen or lumens for blood flow while excluding blood flow to the aneurysm site are introduced into the blood vessel using a catheter in a less or minimally invasive technique. The tubular endoluminal prosthesis is introduced in a small diameter compressed configuration and expanded at the aneurysm. Although often referred to as stent grafts, these tubular endoluminal prostheses differ from so called covered stents in that they are not used to mechanically prop open stenosed natural blood vessels. Rather, they are used to secure graft material in a sealing engagement with the vessel wall and to prop open the tubular passage through the graft without further opening the abnormally dilated natural blood vessel.

Stent grafts for use in abdominal aortic aneurysms typically include a support structure supporting woven or interlocked graft material. Examples of woven graft materials are woven polymer materials, e.g., Dacron, or polytetrafluoroethylene (PTFE). Interlocked graft materials include knit, stretch, and velour materials. The graft material is secured to the inner or outer diameter of the support structure, which supports the graft material and/or holds it in place against a vessel wall. The stent graft is secured to a vessel wall above and below the aneurysm. A proximal spring stent of the stent graft can be located above the aneurysm to provide a radial force to engage the vessel wall and seal the stent graft to the vessel wall.

One problem is that stent grafts can migrate over time after installation in the vessel. The stent graft is subject to a variety of loads due to the force associated with blood flowing through the stent graft, and the pulsatile pressure causing expansion and contraction of arteries. Changes in the anatomy of the abdominal aortic aneurysm can contribute to the cause of migration. One attempt to prevent migration has provided the proximal spring stent with tines, barbs, hooks, and the like to puncture the vessel wall and secure the stent graft in place. Unfortunately, the wall area for prosthesis fixation above an aneurysm or other diseased vessels may be limited, making secure fixation of the prosthesis more difficult. When using hooks, each hook is attached at a single point, so the loading on the vessel wall and the hook is concentrated at the single point. Hydrodynamic loading can dislodge one or more of the hooks from the vessel wall over time and allow migration, exposing the aneurysm to blood pressure and leakage flow. The hooks are also attached to fixed positions spaced around the periphery of the stent graft, so that a poor seal and leakage occurs when the hook is not set to the required depth.

Another problem is that stent grafts can block blood flow to side branches off the vessel in which the stent graft is deployed. For thoracic aortic aneurysms (TAA) in the aortic arch, one or more of the innominate, left common carotid, and left subclavian arteries can be at or near the aneurysm. The location of the arteries can preclude use of a stent graft or limit where the stent graft can be deployed since blood flow to these major arteries must be maintained. The location of the arteries can also limit where hooks can be placed to fix the stent graft to the vessel wall, so that a poor seal and leakage occurs.

It would be desirable to overcome the above disadvantages.

SUMMARY OF THE INVENTION

One aspect according to the present invention provides stent graft for fixation at an attachment site with graft material defining at least one opening having an opening perimeter; a support attached to the graft material; a guide rail attached around the opening perimeter; and a helical anchor having a plurality of coils. The plurality of coils are rotatable around the guide rail to sew the stent graft to the attachment site. Another aspect according to the present invention provides a stent graft system for stent graft fixation at an attachment site including a stent graft; and a driver releasably connected to the helical anchor and having a driver lumen through which a guide tether can slide. The stent graft includes graft material defining at least one side opening having a side opening perimeter; a support attached to the graft material; a guide rail attached around the opening perimeter; a guide tether attached to the guide rail; and a helical anchor having a plurality of coils. The plurality of coils are rotatable around the guide rail to sew the stent graft to the attachment site.

Another aspect according to the present invention provides a method of fixing a stent graft at an attachment site, the method including providing a stent graft; deploying the stent graft with the guide rail aligned with the attachment site; advancing the helical anchor through the stent graft lumen to the attachment site along the guide tether; engaging the helical anchor with the attachment site through the stent graft; and rotating the helical anchor to sew the stent graft to the attachment site along the guide rail. The stent graft has a stent graft lumen and includes graft material defining an opening, the opening having an opening perimeter; a support attached to the graft material; a guide rail attached around the opening perimeter; a guide tether attached to the guide rail; and a helical anchor having a plurality of coils.

The foregoing and other features and advantages will become further apparent from the following detailed description, read in conjunction with the accompanying drawings. The detailed description and drawings are merely illustrative.

BRIEF DESCRIPTION OF THE DRAWINGS

FIGS. 4A-4C are exploded, anchor retracted, and anchor extended views of an anchoring system for a stent graft system;

DETAILED DESCRIPTION

Embodiments according to the invention will now be described by reference to the figures wherein like numbers refer to like structures. The terms "distal" and "proximal" are used herein with reference to the treating clinician during the use of the catheter system: "distal" indicates a delivery system portion distant from, or a direction away from the clinician and "proximal" indicates a delivery system portion near to, or a direction towards the clinician. While for stent graft devices the proximal end is the end closest to the heart by way of blood flow path and the distal end is the end farthest from the heart by way of blood flow path.

Stent graft devices and methods for fixation and sealing of stent grafts are disclosed. While these devices and methods are described below in terms of being used to treat abdominal aortic aneurysms and thoracic aortic aneurysms, those skilled in the art will appreciate that the devices could be used to fix and seal other devices in other vessels as well. Such stent grafts may include stent grafts for fixation at an attachment site, such as a vessel wall circumference and/or a circumostial ring. The systems may further include grafts or stent grafts with helical anchors, and drivers for sewing the grafts or stent grafts to the attachment site with the helical anchors.

Figure 1A:
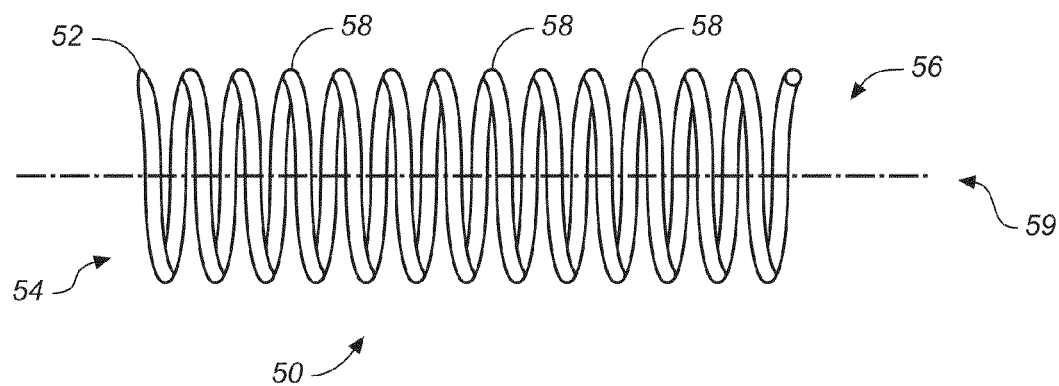
FIGS. 1A & 1B are side and end views, respectively, of a helical anchor for use with a stent graft.
Figure 1B:
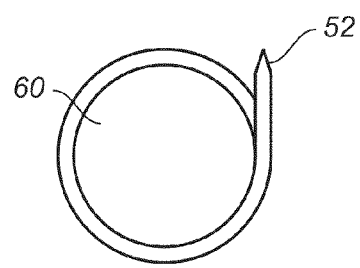

FIGS. 1A & 1B are side and end views, respectively, of a helical anchor. The helical anchor is part of a graft or stent graft system that fixes and seals the graft or stent graft at an attachment site. Helical anchor 50 is an elongated helix having a tissue penetrating sharpened tip 52 at a distal end 54 and a proximal end 56 that can be operably connected to a helical anchor driver. The helical anchor 50 includes a number of individual coils (windings) 58 along a helical anchor axis 59, which form a generally cylindrical inner channel 60 that can accommodate an anchor guide to direct deployment of the helical anchor 50. The helical anchor 50 is rotated about the helical anchor axis 59 when the sharpened tip 52 is engaged with a graft or stent graft and vessel wall tissue to sew the helical anchor 50 to the vessel wall and fix the graft or stent graft in position at an attachment site. The helical anchor axis 59 follows a guide rail about an opening perimeter in the graft or stent graft when the graft or stent graft is fixed in position. The diameter of the inner channel 60, the pitch of the coils 58, and/or the length of the sharpened tip 52 can be selected to provide a desired penetration depth for the helical anchor 50 in the vessel wall tissue. The wire diameter, materials, and pitch of the coils 58 can be selected to provide a desired axial flexibility for the helical anchor 50.

The helical anchor 50 can be formed of a biocompatible metallic or polymeric material having suitable resiliency. The metallic or polymeric material can be a wire coiled to make the helical anchor 50. In one embodiment, the helical anchor 50 is formed of stainless steel. In another embodiment, the helical anchor is formed of 35N LT® metal alloy wire. In yet another embodiment, the helical anchor 50 is formed of MP35N® metal alloy wire. In one embodiment, at least a portion of the helical anchor 50 is made from material having a high X-ray attenuation coefficient to enhance visibility during deployment. In one example, the helical anchor 50 is made of stainless steel wire having a diameter of 0.020 inches, with the helical anchor 50 having an inner diameter of 0.11 inches, an outer diameter of 0.150 inches, and a pitch of 12 coils per inch.

The dimensions and materials of the helical anchor 50 can be selected to provide the desired performance characteristics for a desired application. The coil dimensions and materials can be selected to complement the stiffness, radius, and tortuosity of the guide rail.

The helical anchor 50 forms an inner channel 60 to receive a guide tether and guide rail, which guide the helical anchor 50 during deployment. In one embodiment, the diameter of the inner channel 60 can be in the range of 0.10 inches to 0.20 inches, such as 0.11 inches. In one embodiment, the external diameter of the helical anchor 50 can be in the range of 0.150 inches to 0.250 inches, such as 0.150 inches.

The distance between adjacent coils (windings) 58 defines the coil pitch measured in number of coils per inch. The number of coils per inch for the helical anchor 50 can be selected for the desired degree of flexibility and resiliency. In one embodiment, the coil pitch can be in the range of 10 to 20 coils per inch, such as 12 to 14 coils per inch.

The helical anchor 50 has a generally circular shape transverse to the long axis of the helical anchor 50, and the sharpened tip 52 extends on a tangent away from the circular perimeter of the helical anchor. The sharpened tip 52 is angled away from the exterior circular perimeter of the helical anchor 50 to allow the sharpened tip 52 to penetrate vessel wall tissue when the helical anchor 50 engages the vessel wall at an attachment site. The length of the sharpened tip 52 controls the depth to which the helical anchor 50 penetrates as it is sewn into the vessel wall tissue and depends on the diameter of the coils 58. The length of the sharpened tip 52 also controls resistance to the coil penetration. The length of the sharpened tip 52 is selected for a particular application to be long enough to assure good fixation of the helical anchor 50 to the vessel wall, but not so long that excessive force is required to rotate the helical anchor 50 when sewing the helical anchor 50 to the vessel wall.

The diameter of the metallic or polymeric wire forming the helical anchor 50 can be selected based on design considerations, such as flexibility, delivery method, and the like. In one embodiment, the wire diameter can be in the range of 0.017 inches to 0.025 inches, such as 0.02 inches. The cross section of the wire need not be circular, but can be other shapes as desired. The wire can also include a lubricious coating, such as an MDX coating, for deliverability.

The length of the helical anchor 50 can be selected as desired for the perimeter of the attachment site in the vessel wall available to fix the stent graft. A number of helical anchors can be used with a single stent graft to assure fixation. The helical anchor 50 can have a left hand wind or a right hand wind depending on the particular application.

Figure 2A:
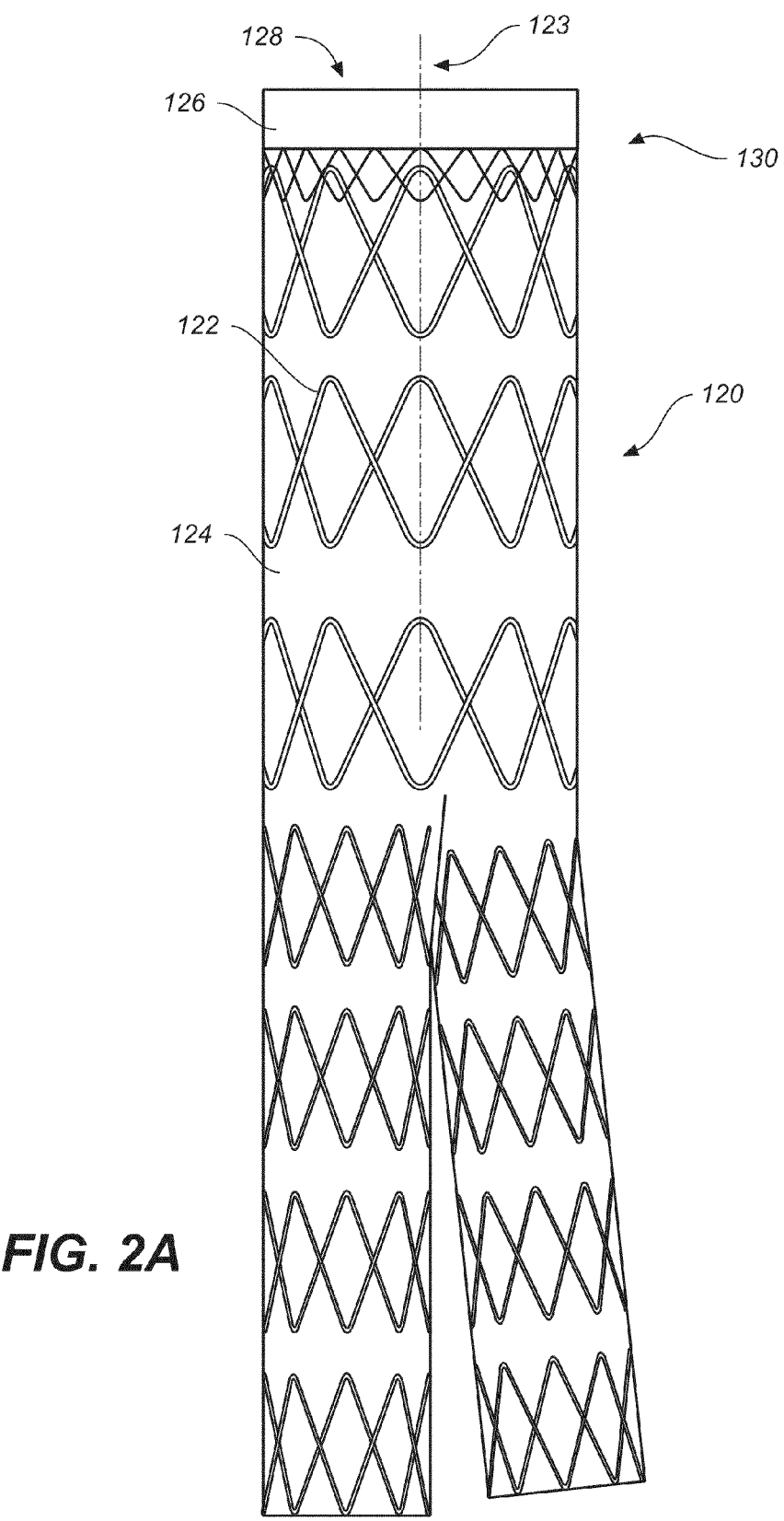
FIGS. 2A-2D are schematic views of stent grafts and portions of stent grafts.
Figure 2B:
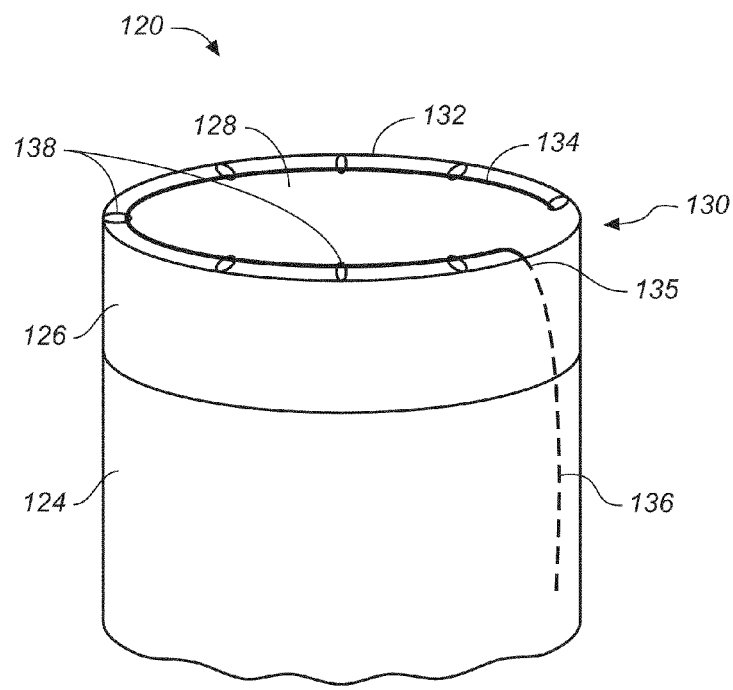
Figure 2C:
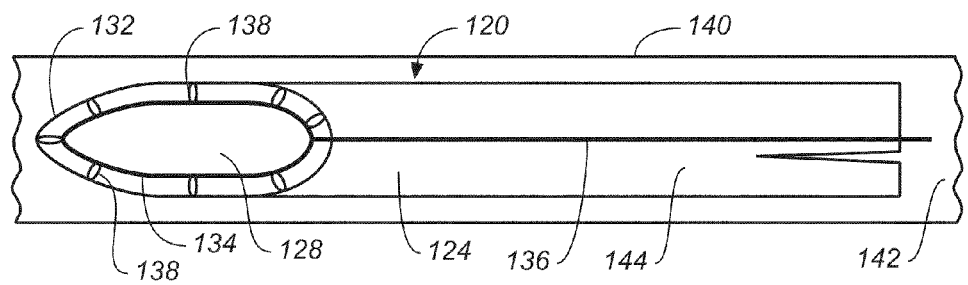
Figure 2D:
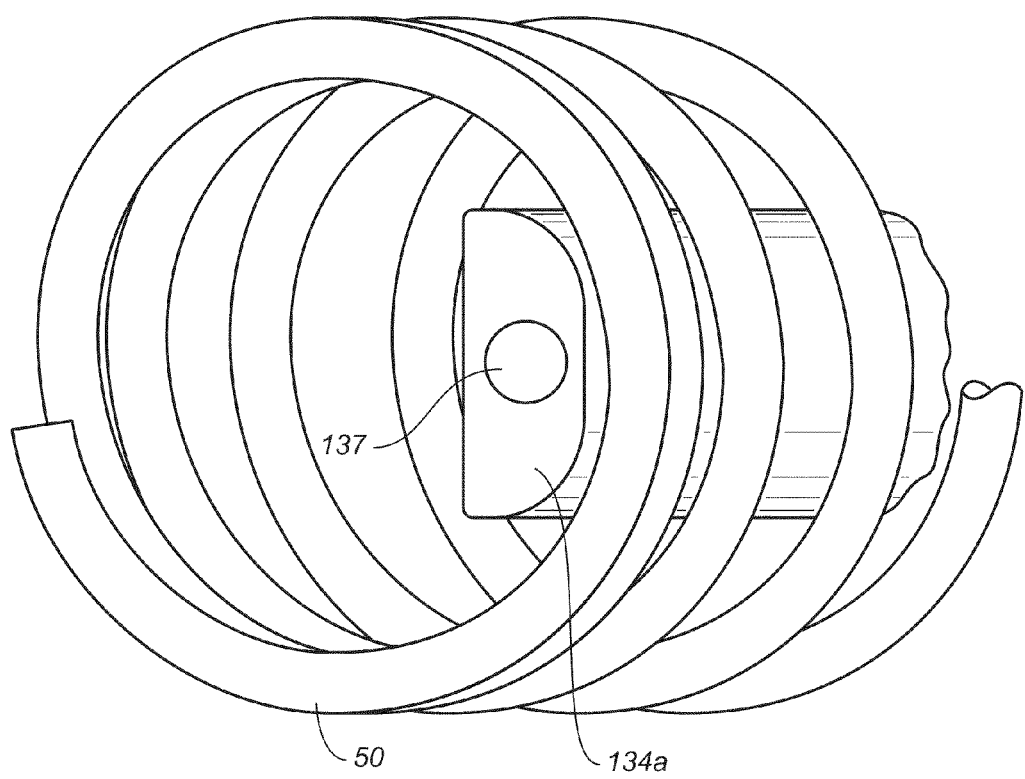

FIGS. 2A-2D are schematic views of a stent graft and portions of stent grafts. FIG. 2A is a fluoroscopic side view of a stent graft in an expanded condition, FIG. 2B is a close up schematic view of the distal end of a stent graft, FIG. 2C is a schematic side view of a stent graft in a compressed condition, and FIG. 2D is a schematic end view of a guide rail and helical anchor.

Referring to FIG. 2A, the stent graft 120 for fixation at an attachment site includes a graft material 124 to which supports 122 are attached. The graft material 124 defines at least one opening 128. In this example, the opening 128 is at the proximal end 130 of the graft material 124. The stent graft 120 has a stent graft axis 123. In one embodiment, the graft material 124 has a felt cuff 126 around the opening perimeter of the opening 128 to facilitate attachment of the helical anchor.

The support 122 can be any suitable device for mechanically keeping a tubular graft open and in sealing contact with healthy surrounding tissue after being implanted at the attachment site, such as the abdominal aorta, thoracic aorta, or other vessel. Such mechanical endoprosthetic devices, sometimes called stent grafts, are typically inserted into the target vessel, positioned across the lesion, and then expanded to bypass the weakened wall of the vessel, thereby preventing rupture of the aneurysm while the graft remains in contact with the healthy tissue after implantation of the graft. The stent graft 120 generally extends across the aneurysm in a vessel in order to divert flow through the stent graft and relieve the pressure from the weak aneurysm wall.

For example, the stent graft 120 may be a self-expanding or balloon expandable stent graft. Although FIG. 2A shows a portion of a bifurcated stent graft, the stent graft 120 may also be a tubular cylindrical stent graft. In one embodiment, the stent graft is expanded by removal of the delivery device constraint after the stent graft is positioned across the aneurysm. The supports 122 used in construction of the stent graft help maintain the expanded shape of the stent graft through mechanical force.

Support 122 is a support having a suitable mechanical configuration for keeping an effective blood vessel open after completion of the stent grafting procedure. For example, the support 122 can be one or more stent type rings attached to graft material 124 and arranged in a manner that will allow stent graft 120 to keep the tubular graft open and in sealing contact with healthy surrounding tissue after implantation. The size and configuration of the support 122 depends upon the size and configuration of the vessel to be treated. If stent type rings are used, the number and size of rings used in the support 122 depends upon the size and configuration of the vessel to be treated. Individual components, such as individual rings of the support 122, can be connected to each other by articulated or rigid joints or can be attached to the graft material 124. The minimum length of the stent graft 120 depends on the size of the aneurysm across which the stent graft 120 will be implanted.

The support 122 can be constructed of one or more suitable implantable materials having good mechanical strength. The material can be deformable or self-expandable to produce the deployed shape for the stent graft 120. For example, support 122 may be made of a suitable biocompatible metal, such as implantable quality stainless steel wire. Alternatively, the support 122 is constructed of nitinol or another suitable nickel titanium alloy. Alternatively, the support 122 is constructed of any suitable metallic, plastic, or biocompatible material. The outside of the support 122 may be selectively plated with platinum, or other implantable radiopaque substances, to provide improved visibility during fluoroscopy. The cross-sectional shape of the finished the support 122 may be circular, ellipsoidal, rectangular, hexagonal, square, or other polygon, depending on the size and shape of the vessel across which the system is implanted.

The stent graft material 124 is constructed of one or more suitable implantable materials having good tensile strength, such as material suitable for resisting expansion when the force associated with blood pressure is applied to it after completion of the stent grafting procedure. For example, the graft material 124 is made of a suitable biocompatible plastic, such as implantable quality woven polyester. In some embodiments, the graft material 124 includes components made of collagen, albumin, an absorbable polymer, or biocompatible fiber. Alternatively, the graft material 124 is constructed from one or more suitable metallic, plastic, or non-biodegradable materials. When the graft material 124 includes a felt cuff 126, the felt cuff can be made of any material that enhances sewing an anchor guide through the graft material 124 by avoiding rolling of the graft material 124 and/or reducing friction as the anchor guide passes through the graft material 124. The felt cuff 126 can be made of polymer materials. In one embodiment, the felt cuff 126 is made of a polymer or copolymer mesh, such as poly(lactic-co-glycolic acid) (PLGA), which swells and expands as it becomes hydrated. The expansion of the felt cuff 126 increases the sealing around the stent graft opening.

The size and configuration of the graft material 124 is selected and sized according to the size and configuration of the aneurysm to be treated. For example, the configuration of the graft material 124 is generally tubular as seen in FIG. 2B. In one embodiment, the graft material 124 is formed of one unitary woven polyester tube. The graft material 124 can be configured to create additional openings in the side of a main tube when the attachment site is in a side surface of the main tube, such as the attachment site as a circum-ostial ring, for example.

FIG. 2B is a schematic close up view of the proximal end of a stent graft. The supports have been omitted from the figure for clarity of illustration. The graft material 124 is configured to provide a tubular opening 128 with an opening perimeter 132, and a guide rail 134 attached around the opening perimeter 132 with connectors 138. In one example, the connectors 138 are wires or rings passing through the graft material 124 and about the guide rail 134. When the graft material 124 includes a felt cuff 126 as shown in FIG. 2B, the connectors 138 attach the guide rail 134 to the felt cuff 126. The connectors attach the guide rail to the main graft body itself when the graft material is a single material omitting the felt cuff. The connectors can be made of any biocompatible metallic or polymeric material. The connection of the graft material 124 to the guide rail 134 can be made by means other than connectors, such as stitching, ultrasonic welding, adhesives, and the like. In this example, a guide tether 136, illustrated by the dashed lines, is inside the graft material 124 and attached to the guide rail 134. The helical anchor having a number of coils is advanced to the attachment site over the guide tether 136 and rotated around the guide rail 134 to sew the stent graft 120 to the attachment site.

The guide tether 136 is shaped to have one or more smooth curves to line up the guide tether 136 with the guide rail 134, so that the helical anchor lines up with and follows the guide rail 134 during attachment of the helical anchor. The force towards the vessel wall from the transition between the guide tether 136 and the guide rail 134, the guide rail 134 and/or the support directs the helical anchor into the vessel wall to initiate sewing. The helical anchor will attempt to follow a straight path, so the guide tether 136 acts as a rail to provide the force required to divert the helical anchor to follow the guide rail 134. Similarly, the guide rail 134 provides an anchor guiding force to keep the helical anchor on its circumferential path as it progresses forward circumferentially and maintains its position around the guide rail 134 and through the associated graft material 124. In this example, the guide rail 134 is circular with a break in the circumference. The guide rail 134 can have other geometric configurations as desired for particular applications, such as a closed circle, a rectangle with radiused corners, or any other outline desired. In another embodiment, the guide rail can be several separate guide rail segments with a separate helical anchor installed on each of the guide rail segments.

The guide rail 134 and guide tether 136 can be formed of a biocompatible metallic or polymeric material having resiliency selected to complement the stiffness of the helical anchor. In one embodiment, the guide rail 134 and/or guide tether 136 is formed of stainless steel. In another embodiment, the guide rail 134 and/or guide tether 136 is formed of 35N LT® metal alloy wire. In yet another embodiment, the guide rail 134 and/or guide tether 136 is formed of MP35N® metal alloy wire. In one embodiment, the guide rail 134 and/or guide tether 136 has a wire core with a fine wire helically wrapped around the wire core. In one embodiment, at least a portion of the guide rail 134 and/or guide tether 136 is made from a radiopaque material, such as platinum, to enhance visibility during deployment.

The guide rail 134 and guide tether 136 are connected to each other so that the guide tether 136 can be removed after the stent graft 120 has been fixed to the attachment site. In one embodiment, the guide tether 136 can be attached to the guide rail 134 with a fusible link 135. A current from a current source can be passed through the guide tether 136 and guide rail 134 after the stent graft 120 has been fixed to the attachment site to melt the fusible link 135. A low voltage current, such as a current driven by about 9 Volts, can pass from the proximal end of the guide tether 136, through body of the patient, to an electrode patch secured on the exterior of the patient near the attachment site. The resistance heating of the fusible link 135 causes the fusible link to melt. The current path can include an impedance monitor to determine when the fusible link opens. The fusible link 135 can be made of a lead-free solder, such as a solder including silver and tin. In another embodiment, the guide tether 136 can be clipped off near the guide rail 134 with a cutter that is part of the distal end of the driver or anchor guide and the guide tether removed.

FIG. 2C is a schematic side view of a stent graft in a compressed condition. The stent graft 120 can be compressed to allow the stent graft 120 to be held within a catheter 140 as it is advanced to an attachment site. The guide rail 134 is compressed to an oval, elliptical, or other compressed shape to reduce the diameter and allow the guide rail 134 to be contained within the catheter 140. When the guide rail 134 is deployed from the catheter 140 at the attachment site, the guide rail 134 assumes a desired final shape through resiliency or shape memory of the guide rail 134. The guide tether 136 is attached to the guide rail 134 and is threaded through the stent graft lumen 144 back to the proximal end of the catheter. The shape in the compressed condition and the diameter achieved depends on the particular stent graft design and the folding method.

FIG. 2D is a schematic sectional view of a guide rail and surrounding helical anchor. In this embodiment, the guide rail 134a is D-shaped (semicircular—though a rectangle with two rounded corners is shown in FIG. 2D), with the radiused portion of the D-shape contacting the inner circumference of the helical anchor 50. In this example, the guide rail 134a includes a core 137. The guide rail 134a urges the helical anchor 50 to a position close to the graft material so that as the helical anchor is rotated it moves around the stent graft when sewing the helical anchor 50 to the graft material 124 and vessel wall. The stiffness of the guide rail is selected to complement the stiffness of the helical anchor, so the helical anchor follows the guide rail during helical anchor attachment. A semi-circular D-shape guide rail is sized to have a cross sectional area that is approximately 25% of the cross sectional area of the approximately circular inner diameter of the helical anchor (FIG. 2D is not to scale).

Figure 3A:
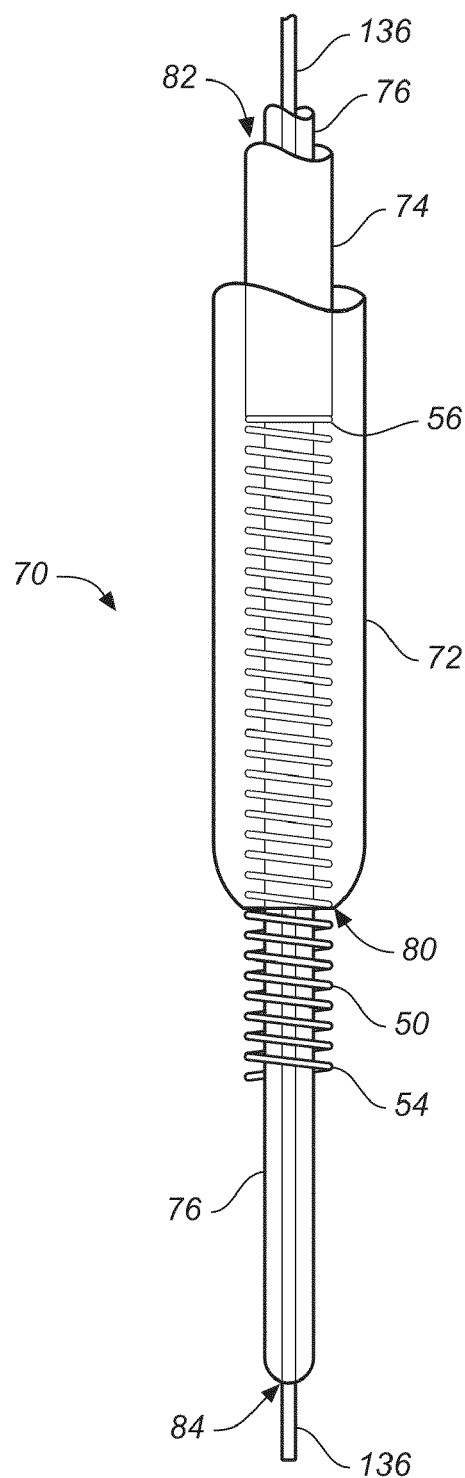
FIGS. 3A & 3B are close up proximal and distal end views, respectively, of portions of an anchoring system for a stent graft system.
Figure 3B:
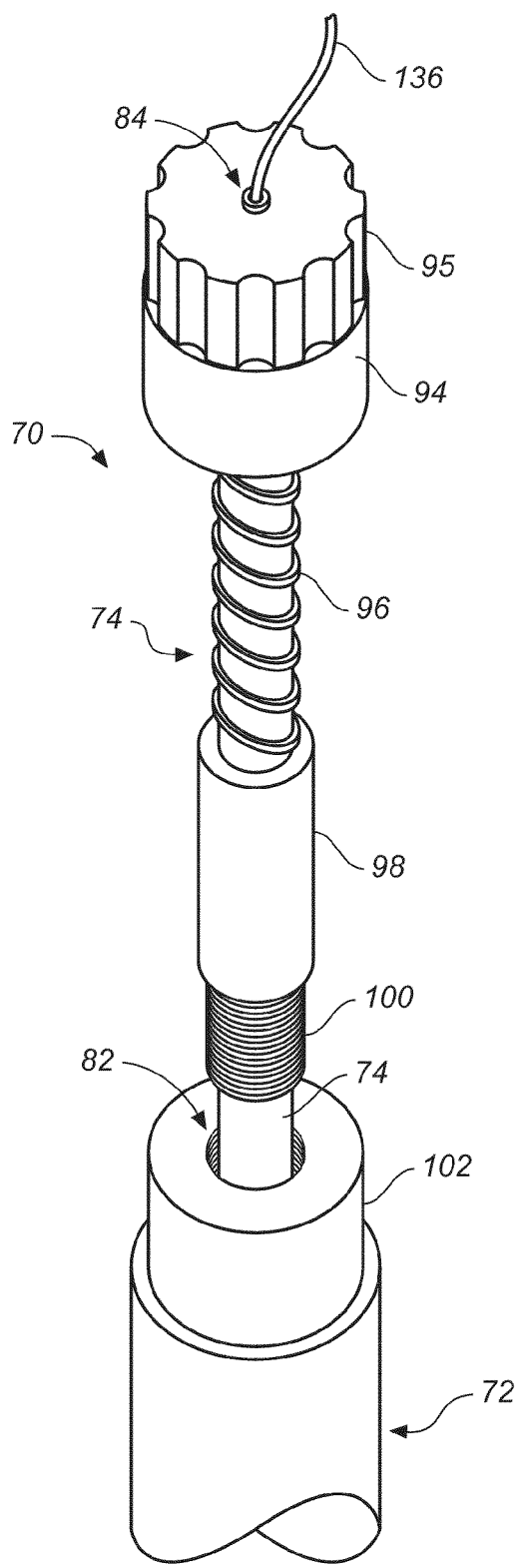
Figure 4A:
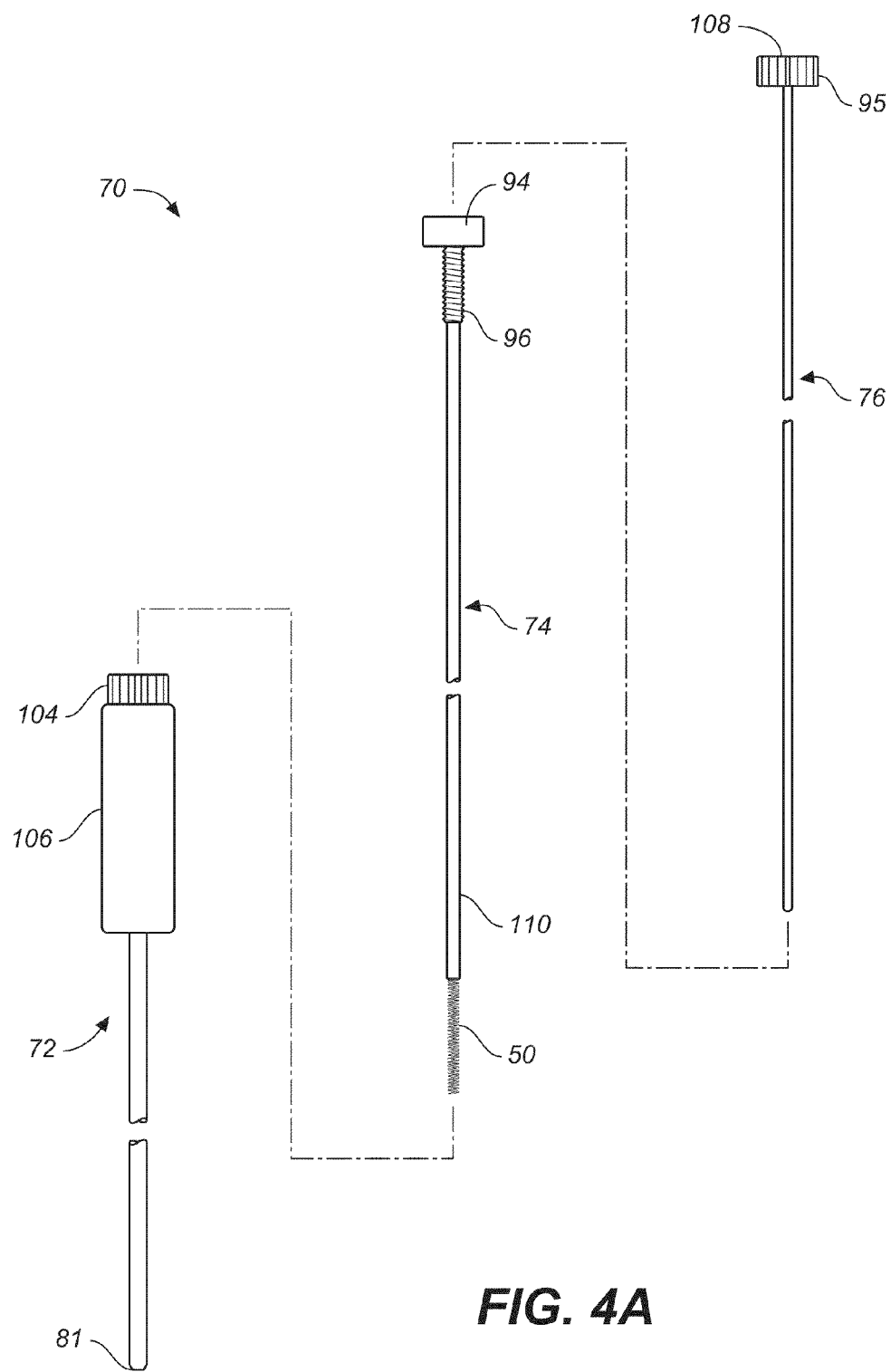

FIGS. 3A, 3B, & 4A-4C are views of an anchoring system for a stent graft system. FIGS. 3A & 3B show close up views of the distal and proximal ends, respectively, of a helical anchor delivery system for the stent graft system. FIGS. 4A-4C illustrate exploded, anchor retracted, and anchor advanced configurations, respectively, of a helical anchor delivery system for the stent graft system. The helical anchor delivery system advances the helical anchor over the guide tether and rotates the helical anchor around the guide rail to sew the stent graft to the attachment site.

Referring to FIG. 3A, the delivery system 70 for the helical anchor 50 includes a delivery catheter 72, driver 74, and anchor guide 76. The delivery catheter 72 is a flexible elongate tube for insertion into the patient. The delivery catheter 72 includes a catheter lumen 80 for receiving the driver 74 and the anchor guide 76. The delivery catheter 72 can be made of flexible, biocompatible polymeric material such as, but not limited to, polyurethane, polyethylene, nylon, and polytetrafluoroethylene (PTFE).

The driver 74 is an elongate tube having a distal drive end for driving the helical anchor 50. The driver 74 is able to rotate and translate longitudinally along a long axis of the catheter lumen 80 during implantation of the helical anchor 50. The distal end of the driver 74 includes a helical anchor-receiving portion for releasably holding the helical anchor 50. In one embodiment, the helical anchor-receiving portion includes a hole for receiving a pin-shaped driver portion of the proximal end of the helical anchor 50 as described for FIG. 6. In another embodiment, the helical anchor-receiving portion includes a surface indentation or slot for receiving a generally U-shaped driver portion of the proximal end of the helical anchor 50 as described for FIG. 5A. In another embodiment, the helical anchor-receiving portion includes an indentation or slot for receiving a generally wrapping driver portion of the proximal end of the helical anchor 50 as described for FIG. 5B. In one embodiment, the driver 74 includes a driver lumen 82 for receiving the anchor guide 76. The driver 74 can be made of flexible, biocompatible polymeric material such as, but not limited to, polyurethane, polyethylene, nylon, and polytetrafluoroethylene (PTFE). In one embodiment, the interior walls of the delivery catheter 72 forming the catheter lumen 80 are coated with a lubricious material such as silicone, polytetrafluroethylene (PTFE), or a hydrophilic coating. The lubricious interior walls of the delivery catheter 72 facilitate longitudinal movement of the driver 74.

The anchor guide 76 is an elongate member configured to place the helical anchor 50 at the attachment site in the vessel wall during deployment. The anchor guide 76 can be made of a biocompatible metallic or polymeric material or combinations thereof. Fabrication of the anchor guide 76 can include chemical machining, forming, and/or heat setting of nitinol. The anchor guide 76 includes a tether lumen 84 through which the guide tether 136 can slide. The distal end of the guide tether 136 is attached to the guide rail of the stent graft as described above. The distal end of the anchor guide 76 can be shaped and/or curved to facilitate positioning of the helical anchor 50 at the attachment site.

The anchor guide 76 can have a generally circular or elliptical cross-section such that at least a portion of the exterior surface of the anchor guide 76 has a shape that is complementary to the inner circumference of the helical anchor 50. During deployment of helical anchor 50, the helical anchor 50 releasably connected to the driver 74 slides over the anchor guide 76.

During the delivery of a helical anchor 50 to an attachment site, the various components of the system are concentrically disposed within the delivery catheter 72. The arrangement of the various components within the delivery catheter 72 can be selected as desired for a particular application.

FIG. 3B illustrates the proximal end of the delivery system 70 with controls for manipulating the various components of the delivery system 70. The proximal end of the driver 74 includes an anchor driver knob 94, a threaded portion 96, and an optional lock ring 98. The lock ring 98 includes a threaded section 100 for threaded engagement with a delivery catheter ring 102. The lock ring 98 holds the threaded section 100 to the delivery catheter 72 during implantation of the helical anchor 50. In another embodiment, the lock ring 98 can be omitted and the threaded portion 96 of the driver 74 engages threads in the delivery catheter ring 102 directly. The anchor guide 76 includes a guide driver knob 95.

To deploy the helical anchor 50, the delivery system 70 is preloaded with the anchor guide 76 installed within the driver 74 which is installed within the delivery catheter 72. The guide tether 136 attached to the guide rail of the stent graft is threaded through the anchor guide 76. The lock ring 98 is screwed into the handle cap 102 with the threaded section 100. The distal tip of the anchor guide 76 and the helical anchor 50 on the driver 74 are placed at the attachment site. As the driver knob 94 is turned it screws the threaded portion 96 of the driver 74 into the interior of the lock ring 98 and the driver 74 turns the helical anchor 50 to sew it into adjacent structures such as the graft material and the vessel wall.

The guide tether 136 can be detached from the guide rail once the helical anchor 50 has been implanted. The driver 74 can then be disengaged from the helical anchor 50 and the delivery system 70 withdrawn from the patient. The order of detachment and withdrawal can be selected as desired for a particular application.

FIGS. 4A-4C are exploded, anchor retracted, and anchor extended views, respectively, of a helical anchor delivery system for the stent graft system.

Referring to FIG. 4A, the delivery catheter 72 is an elongated generally tubular catheter having a handle 106 and a handle cap 104 at the proximal end of the delivery catheter 72. The delivery catheter 72 includes a catheter lumen (not shown) which extends the axial length of the delivery catheter 72 to an exit at distal opening 81. A helical anchor driver 74 can be disposed in the driver lumen.

The elongated helical anchor driver 74 includes a driver knob 94 on the proximal end of the driver 74 and a threaded portion 96 adjacent the driver knob 94. A distal end 110 of the driver 74 is releasably connected to a helical anchor 50. The driver 74 includes a driver lumen (not shown) through its axial length. An anchor guide 76 can be disposed in the driver lumen. The driver 74 can be made from any biocompatible material allowing the driver 74 to rotate and to move longitudinally inside of the delivery catheter 72, and carry a rotational and axial load from its proximal end to the helical anchor 50.

The anchor guide 76 includes a guide driver knob 95 on the proximal end of the anchor guide 76. The anchor guide 76 includes a tether lumen (not shown) through its axial length. The guide tether (not shown) can be disposed in the tether lumen in the anchor guide 76. One end of the guide tether remains outside the patient's body during the implantation procedure and the other end is attached to the guide rail of the stent graft. From the distal end the guide tether 136 with or without the anchor guide 76 passes through helical anchor 50 and exits a driver opening 108 of the tether lumen at the proximal end of the anchor guide 76. The delivery catheter 72, driver 74, and anchor guide 76 are flexible enough to negotiate the turns and curves required for an approach to a attachment site through a patient's vasculature.

Referring to FIG. 4B, the exploded pieces having been assembled, the driver 74 is positioned in the catheter lumen of the delivery catheter 72 and the anchor guide 76 is positioned in the driver lumen of the driver 74. In this embodiment, the threaded portion 96 of the driver 74 directly engages a complementary threaded portion (not shown) in the handle cap 104. The anchor guide 76 is advanced until the distal tip of the anchor guide 76 is at the attachment site.

Referring to FIG. 4C, the driver knob 94 is rotated so that the threaded portion 96 on the driver 74 is screwed into the complementary threaded portion of the delivery catheter 72. As the driver 74 is threaded into the delivery catheter 72, the distal portion of the driver 74 rotates and moves toward the distal opening 81 of the delivery catheter so that the distal end of the helical anchor 50 exits the delivery catheter 72 and engages the targeted structures, e.g., the vessel wall. The continued rotation of the driver knob 94 continues to progressively sew the helical anchor 50 into the vessel wall around the guide rail at the attachment site. In one embodiment, contact between the driver knob 94 and the handle cap 104 acts as a stop to limit the rotation of the driver knob 94 and axial travel of the helical anchor 50. In another embodiment, the threaded portion 96 on the driver 74 is omitted and the rotation and advancement of the driver 74 within the delivery catheter 72 is controlled manually by the clinician. In yet another embodiment, the helical anchor 50 is delivered to the attachment site by the driver 74 through a catheter and implanted without the use of an anchor guide: the driver 74 passes about the guide tether 136 alone. The distal portion of the delivery system for handling and operating can be any arrangement desired for a particular application as long as the delivery catheter 72, driver 74, and anchor guide 76 are free to slide axially relative to one another and the driver 74 is free to rotate relative to the delivery catheter 72 and anchor guide 76.

Figure 5A:
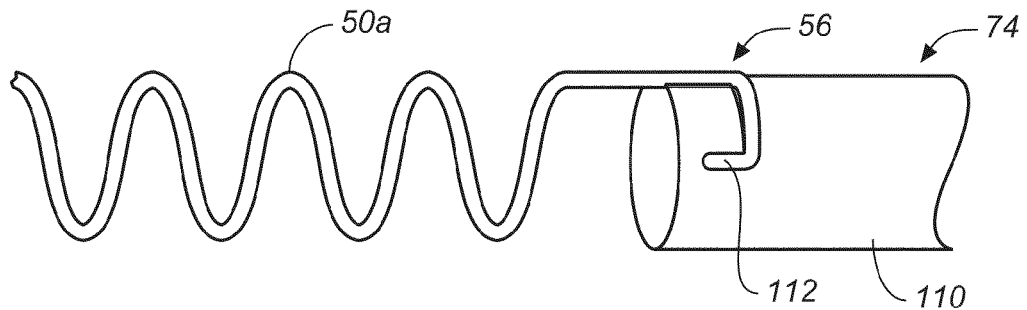
FIGS. 5A, 5B, and 6 are illustrations of helical anchors attachment to helical anchor drivers.
Figure 5B:
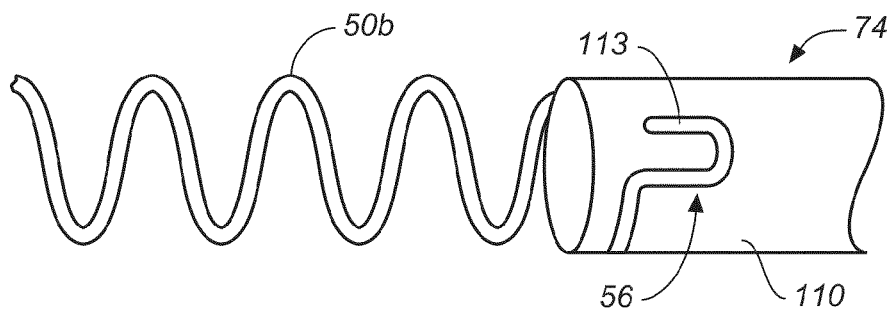
Figure 6:
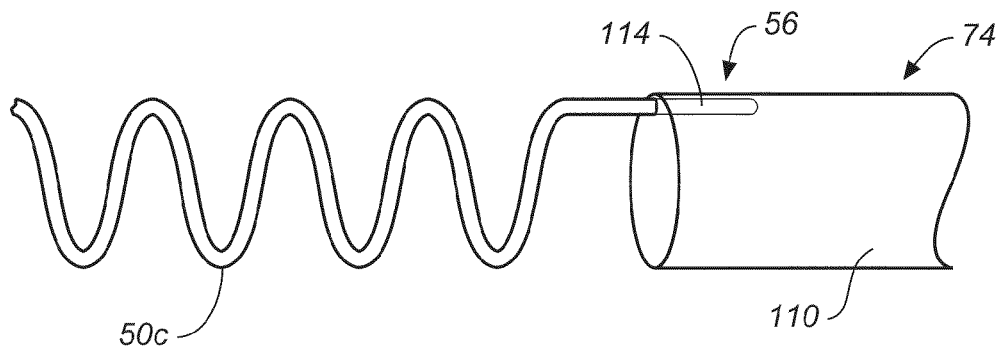

FIGS. 5A, 5B, and 6 are side views of partial portions of helical anchors attached to a helical anchor driver. FIG. 5A illustrates one embodiment of a release mechanism in which the helical anchor 50a has a generally U-shaped driver portion 112 at the proximal end 56 of the helical anchor 50a. The distal end 110 of the driver 74 includes an indentation that is sized and shaped so that the driver portion 112 at the proximal end 56 of the helical anchor 50a fits snugly into the driver 74 for delivery of the helical anchor 50a. A retractable sleeve (not shown) is disposed over the driver portion 112 and the sleeve is retracted to free the helical anchor 50a from the driver 74 once the helical anchor 50a is fully attached to the vessel wall. The driver portion, complementary indentation, and sleeve can be on the inside or outside circumference of the driver 74 as desired for a particular application. In one embodiment, the sleeve is the distal end of the delivery catheter 72.

FIG. 5B illustrates an embodiment of a release mechanism in which the helical anchor 50b has a generally wrapping driver portion 113 at the proximal end 56 of the helical anchor 50b. The distal end 110 of the driver 74 includes an indentation that is sized and shaped so that the driver portion 113 at the proximal end 56 of the helical anchor 50b fits snugly into the driver 74 for delivery of the helical anchor 50b. Part of the helical portion of the helical anchor 50b fits into the indentation as well, so that the helical portion wraps around the distal end 110 of the driver 74. A retractable sleeve (not shown) is disposed over the driver portion 113 and the sleeve is retracted to free the helical anchor 50b from the driver 74 once the helical anchor 50b is attached to the vessel wall. The driver portion, complementary indentation, and sleeve can be on the inside or outside circumference of the driver 74 as desired for a particular application. In one embodiment, the sleeve is the distal end of the delivery catheter 72.

FIG. 6 illustrates another embodiment of a release mechanism in which the helical anchor 50c has a pin-shaped driver portion in a proximal end 56 with a driver portion 114 that extends straight in a proximal direction from the helical anchor 50c. The distal end 110 of the driver 74 includes a hole for placement of the driver portion 114 of the helical anchor 50c such that the driver portion 114 fits snugly into the driver 74 during implantation. Once the helical anchor 50c is implanted, the driver 74 is retracted axially without rotation from the helical anchor 50c and the straight driver portion 114 of the proximal end 56 is pulled from the hole in the distal end 110 of the driver 74. In one embodiment, the length of the straight driver portion 114 of the helical anchor 50c can be in the range of 0.05 inches to 0.25 inches, such as 0.10 inches.

In another embodiment, the release mechanism for the helical anchor can be a fusible link between the helical anchor and the distal end of the driver. A current from a current source can be passed through the driver after the stent graft has been fixed to the attachment site to melt the fusible link. A low voltage current, such as a current driven by about 9 Volts, can pass from the proximal end of the driver, through body of the patient, to an electrode patch secured on the exterior of the patient near the attachment site. The resistance heating of the fusible link causes the fusible link to melt. The current path can include an impedance monitor to determine when the fusible link opens. The fusible link can be made of a lead-free solder, such as a solder including silver and tin.

Figure 7A:
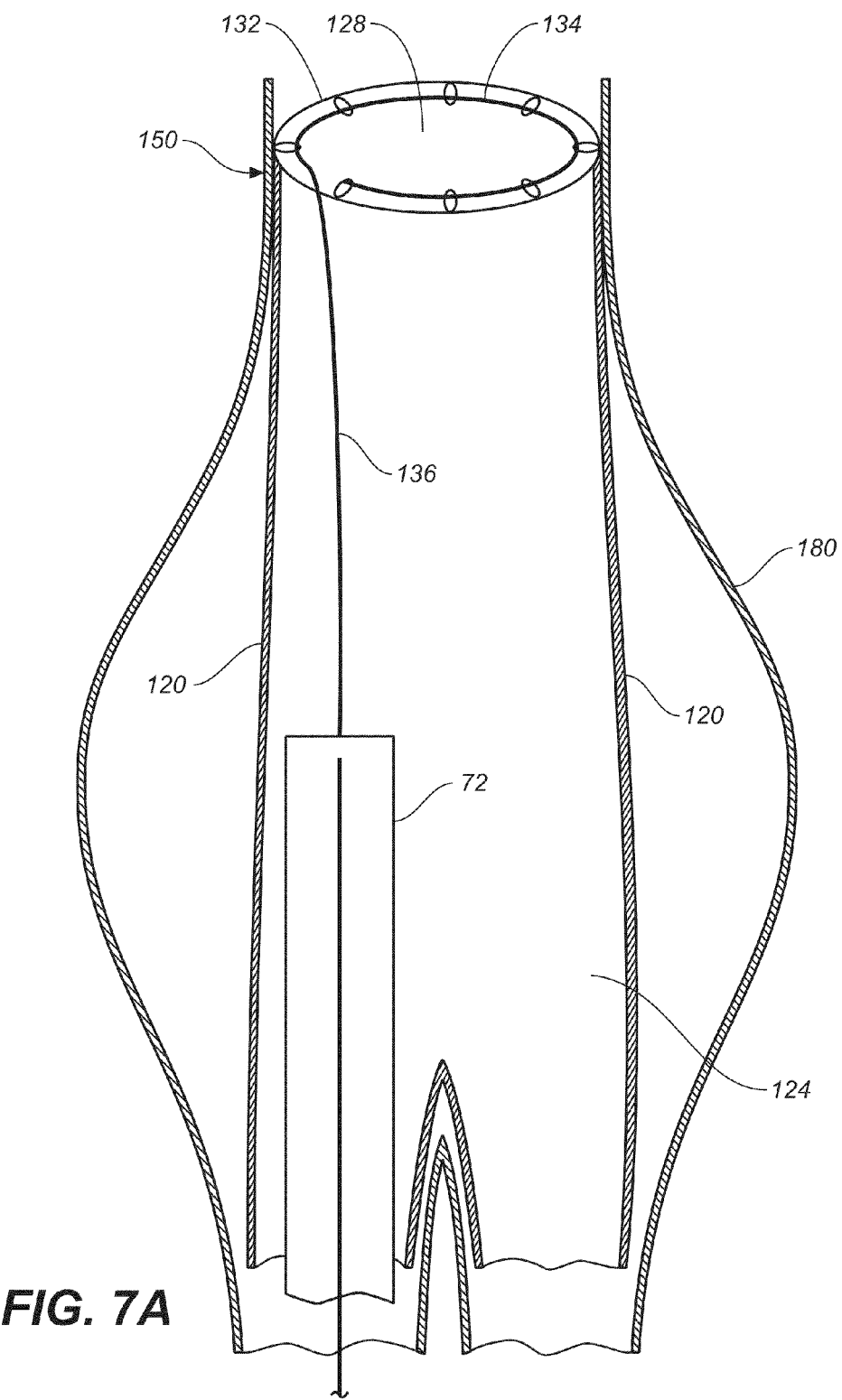
FIGS. 7A-7F are schematic views of deployment of a helical anchor at the proximal end of a stent graft.
Figure 7B:
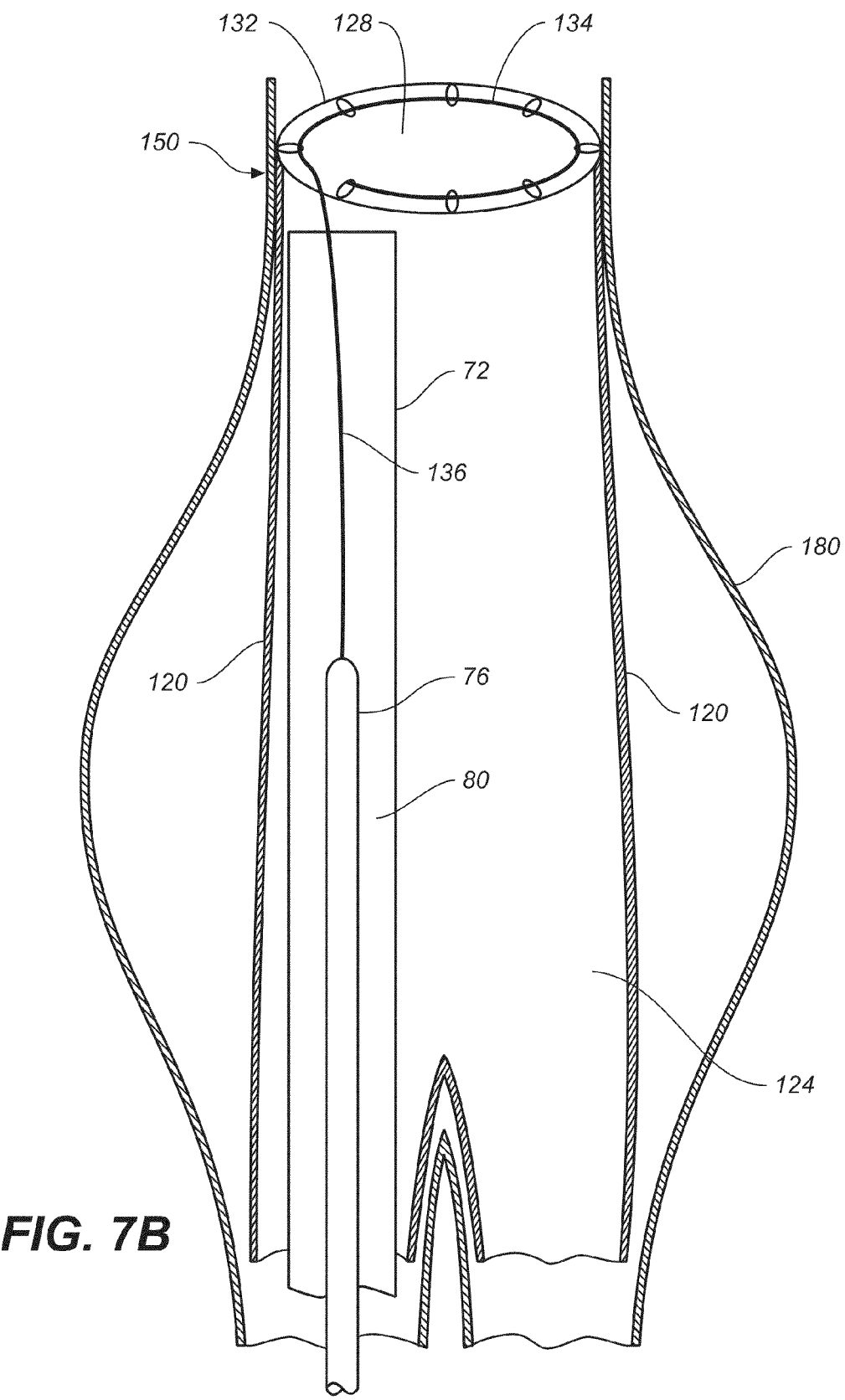
Figure 7C:
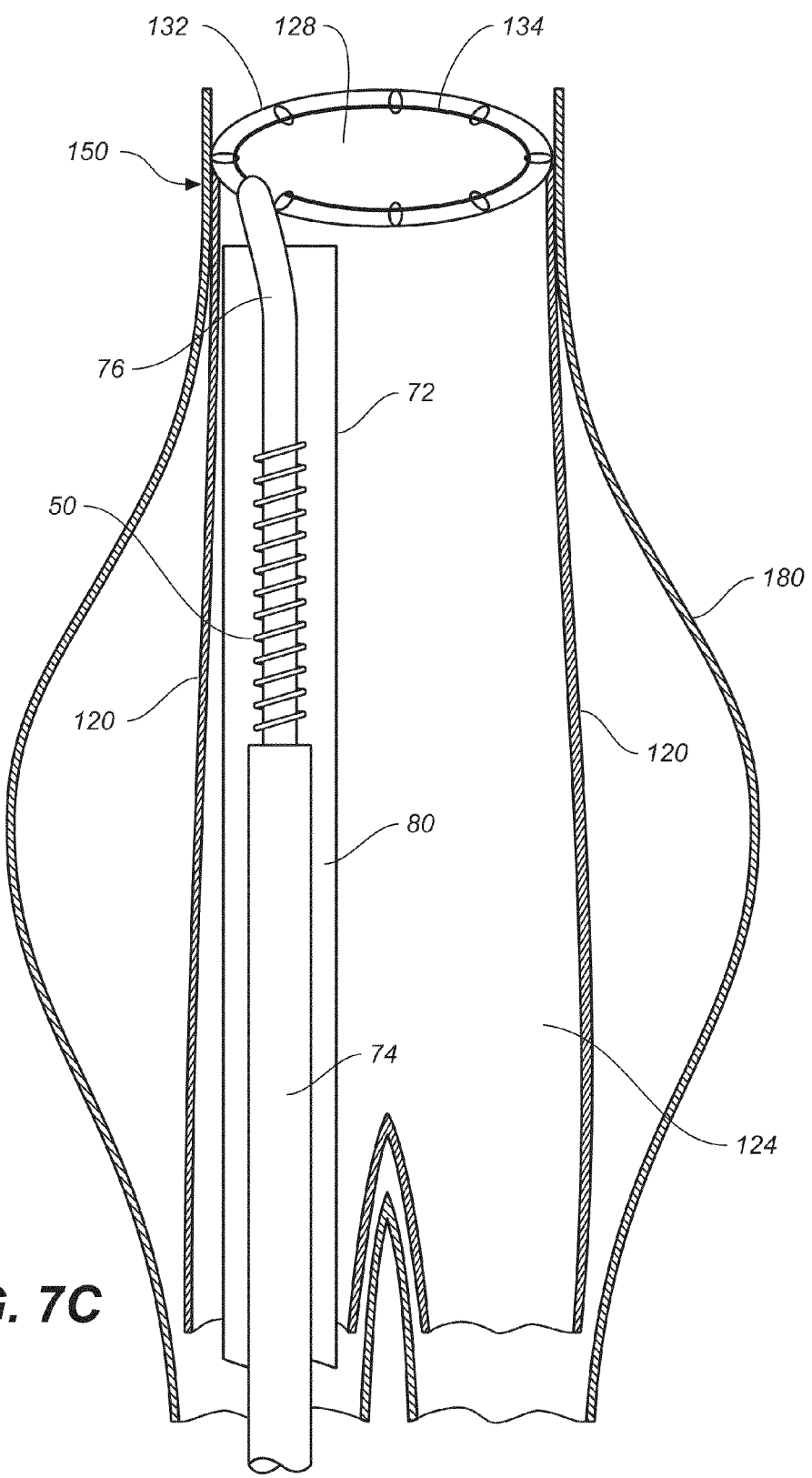

FIGS. 7A-7F are schematic views of deployment of a helical anchor at the proximal end of a stent graft. The supports of the stent graft have been omitted from the figures for clarity of illustration. Referring to FIG. 7A, the stent graft 120 has been deployed in an aneurysm 180 with the guide rail 134 aligned with the attachment site 150. In this example, the guide rail 134 is circular with a break in the circumference. The delivery catheter 72 advances into the stent graft 120 over the guide tether 136. Referring to FIG. 7B, the distal end of the delivery catheter 72 has been positioned adjacent to the attachment site 150. An anchor guide 76 is advanced toward the attachment site 150 through the catheter lumen 80. Referring to FIG. 7C, the distal end of the anchor guide 76 has been positioned adjacent to the attachment site 150. A helical anchor 50 releasably connected to a driver 74 is advanced toward the attachment site 150 through the catheter lumen 80. The guide rail 134 guides the helical anchor 50 in close proximity to the vessel wall. As the sharpened tip 52 of the helical anchor 50 is exposed from the delivery catheter 72, the tip engages the adjacent structures and penetrates progressively more deeply with every angular degree of rotation of the helical anchor 50. The size and orientation of the guide rail 134 prevents the path sewn by the helical anchor from plunging completely through the surface and thickness of the graft material and vessel into surrounding anatomical structures. The guide rail essentially acts as a side stop to guide the helical anchor around a sewing path at the surface of the fabric wall of the stent graft and vessel.

Figure 7D:
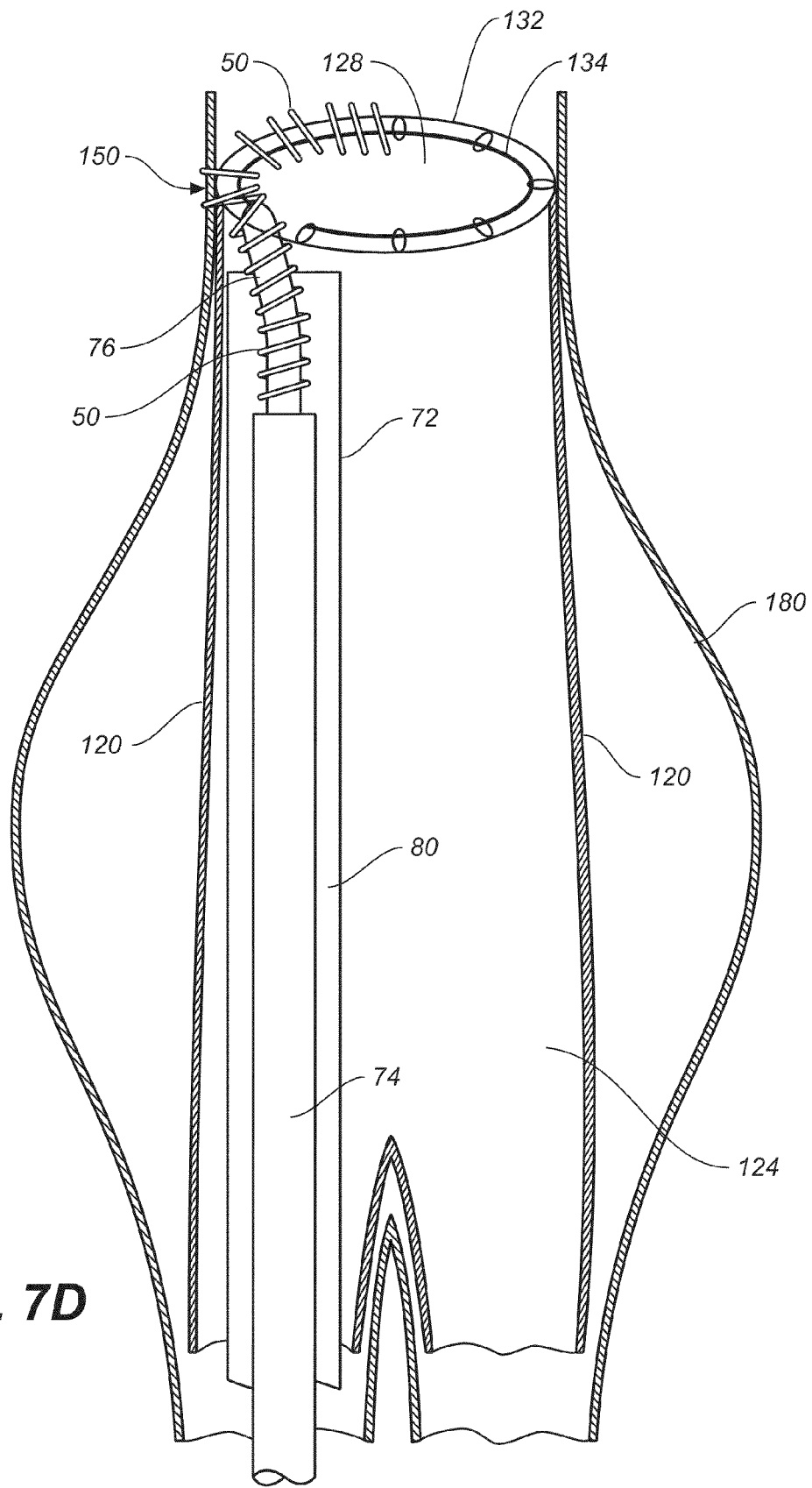
Figure 7E:
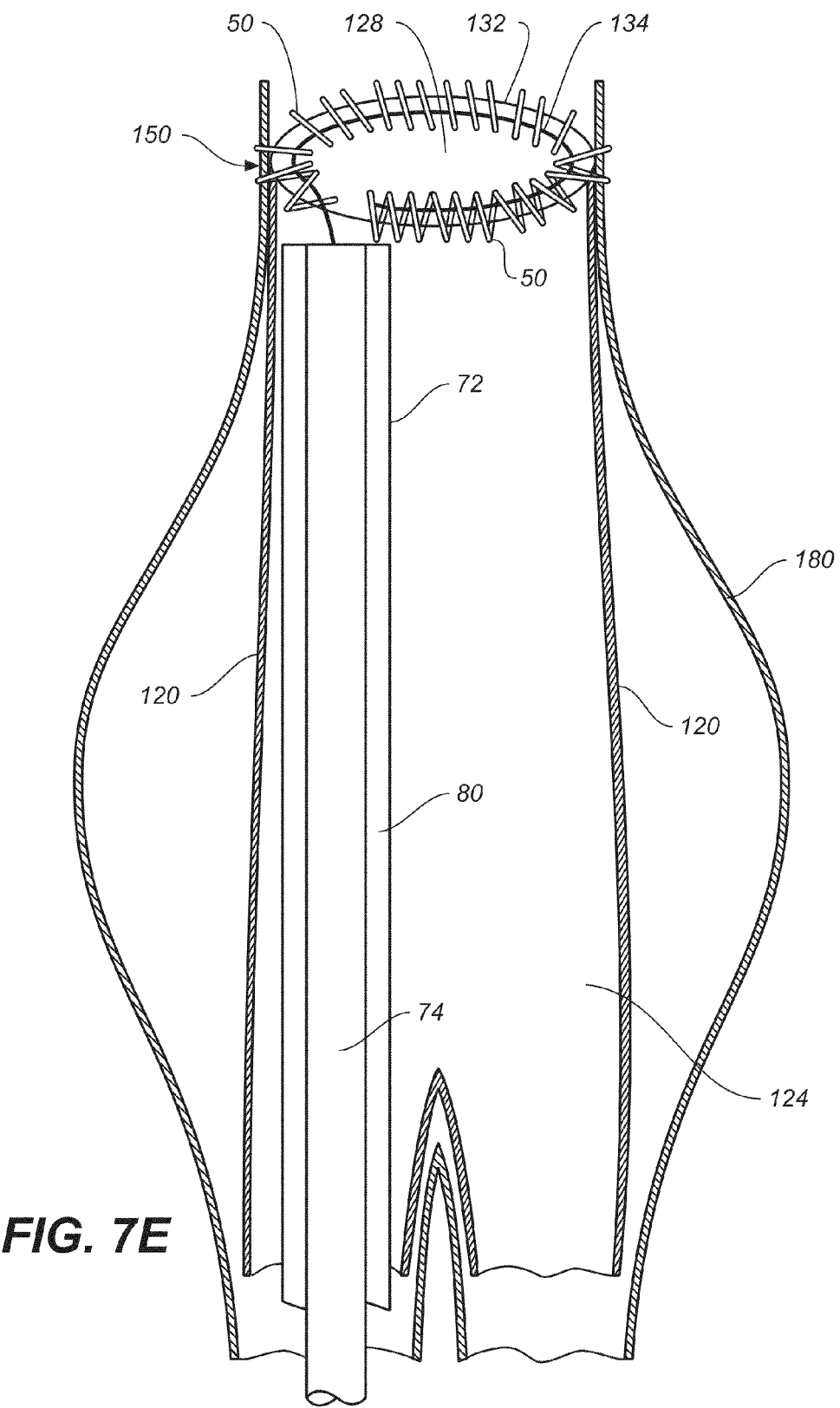
Figure 7F:
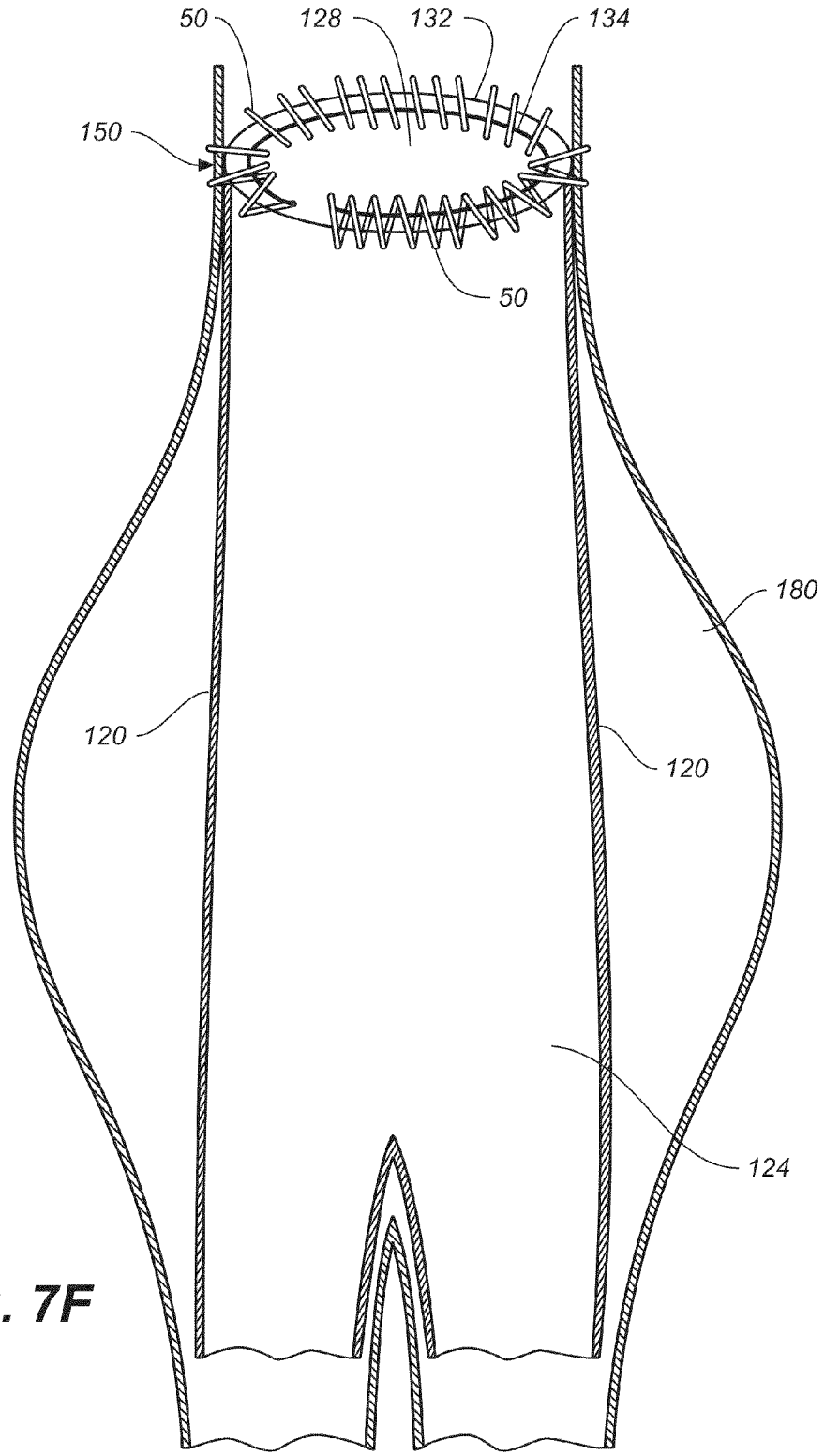

Referring to FIG. 7D, the helical anchor 50 is illustrated partially deployed at the attachment site 150. The helical anchor 50 has been rotated and advanced by the driver 74 to engage the attachment site 150 in the vessel wall. The helical anchor 50 engages the attachment site 150 in the vessel wall through the fabric wall of the stent graft 120. The rotation of the helical anchor 50 around the guide rail 134 sews the stent graft to the attachment site 150 along the guide rail 134. Referring to FIG. 7E, the helical anchor 50 is illustrated fully deployed at the attachment site 150. The helical anchor 50 engages the attachment site 150 in the vessel wall through the stent graft 120, with the helical anchor 50 encircling the opening 128 of the graft material 124. Referring to FIG. 7F, the deployment has been completed. The driver 74 has been detached from the helical anchor 50 and withdrawn. The guide tether 136 has been detached from the guide rail 134.

Figure 8:
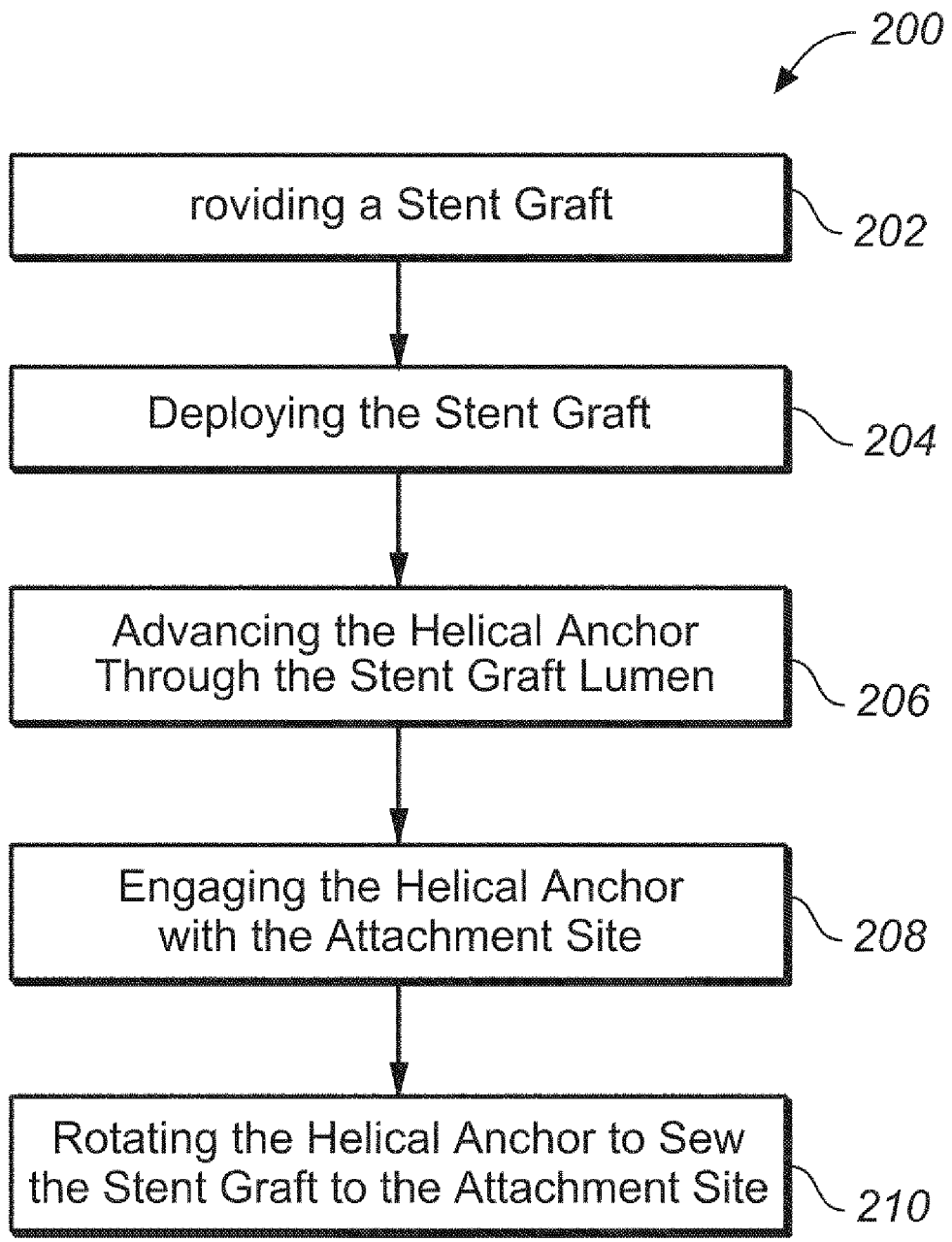
FIG. 8 is a flowchart of the steps of a method of fixing a stent graft at an attachment site.

FIG. 8 is a flowchart of the steps of a method of fixing a stent graft at an attachment site. The method 200 includes the steps of providing a stent graft (202) including graft material defining an opening having an opening perimeter; a support attached to the graft material; a guide rail attached around the opening perimeter; a guide tether attached to the guide rail; and a helical anchor having a number of coils. The method 200 further includes the steps of: deploying the stent graft (204) with the guide rail aligned with the attachment site; advancing the helical anchor through the stent graft lumen (206) to the attachment site along the guide tether; engaging the helical anchor with the attachment site (208) through the stent graft; and rotating the helical anchor to sew the stent graft to the attachment site (210) along the guide rail. In one embodiment, the method 200 can further include the step of detaching the guide tether from the guide rail. In one embodiment, the guide tether is attached to the guide rail with a fusible link, and the method 200 further includes the step of detaching the guide tether from the guide rail by melting the fusible link.

In one embodiment, the method 200 further includes the steps of providing a driver releasably connected to the helical anchor and having a driver lumen through which the guide tether can slide; providing a delivery catheter having a catheter lumen through which the driver can slide; and providing an anchor guide having a tether lumen through which the guide tether can slide. The step of advancing the helical anchor through the stent graft lumen (206) includes the sub-steps of advancing the delivery catheter into the stent graft lumen; advancing the anchor guide within the catheter lumen along the guide tether to the attachment site; and advancing the helical anchor within the delivery catheter along the anchor guide to the attachment site.

Figure 9:
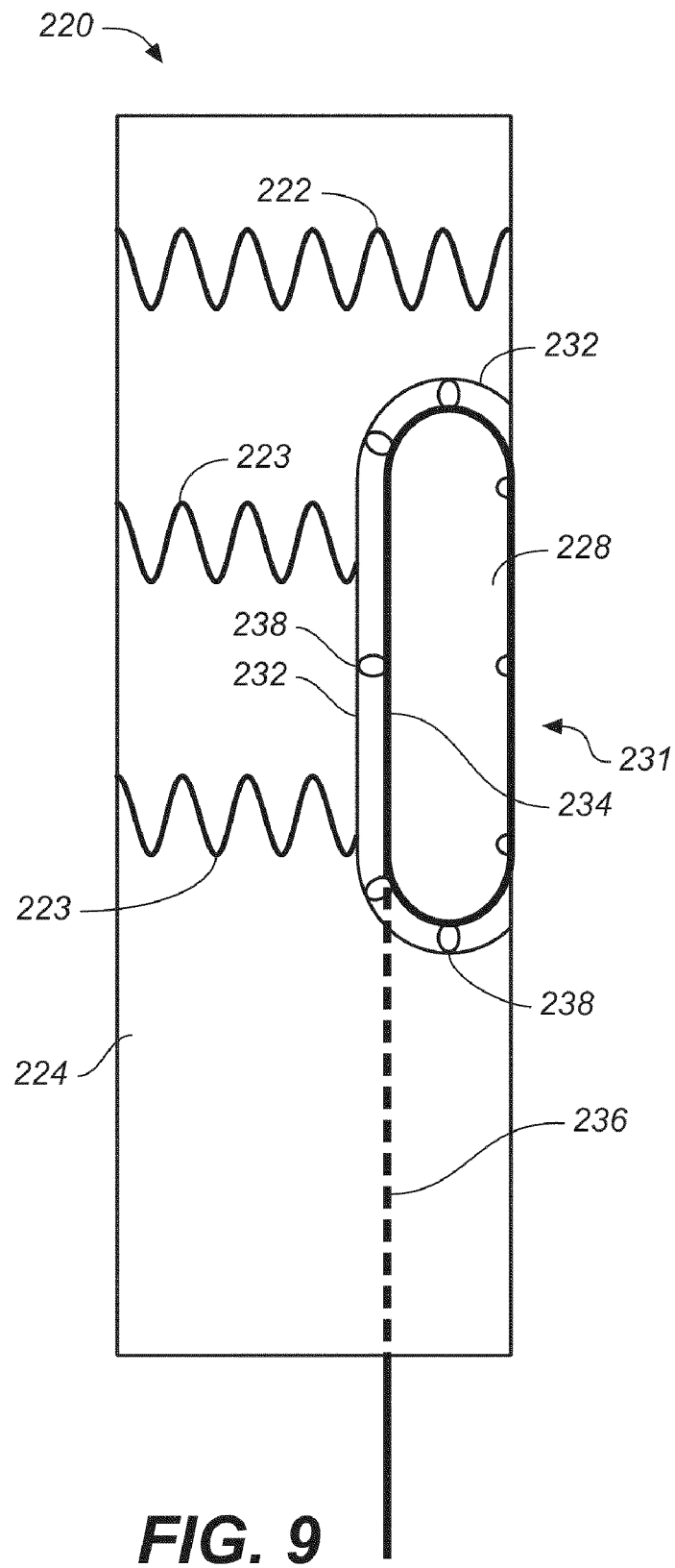
FIG. 9 is a schematic side view of another embodiment of a tubular stent graft.

FIG. 9 is a side view of another embodiment of a tubular stent graft having an opening in a side of the tube. The attachment site in this embodiment is a circum-ostial ring encircling at least one ostium of a branch vessel. The helical anchor sews the side opening of the stent graft in place about the circum-ostial ring, so as to provide an opening for blood flow to side branches of the main vessel in which the stent graft is deployed. The stent graft and stent graft system are similar to that described above for the stent graft of FIGS. 2A-2C, with the addition of a guide rail about an opening in the side of the graft material. The stent graft can be attached to the vessel both at the end and side as desired for a particular application.

Referring to FIG. 9, the stent graft 220 includes tubularly configured graft material 224 to which supports 222 are attached, with at least one opening 228 in the side of the tube having an opening perimeter 232. In this example, the opening 228 is in the side 231 of the graft material 224. In one embodiment, the graft material 224 has a felt cuff around the opening perimeter 232. A guide rail 234 is attached around the opening perimeter 232 of the graft material 224 with connectors 238. In one example, the connectors 238 are wires or rings passing through the graft material 224 and about the guide rail 234. The connection of the graft material 224 to the guide rail 234 can be made by means other than connectors, such as stitching, ultrasonic welding, adhesives, and the like. In one embodiment, the guide rail 234 is also attached to one or more of the guide rail supports 223, which can optionally be attached to the graft material 224. A guide tether 236 inside the graft material 224, illustrated by dashed lines, is attached to the guide rail 234. The helical anchor having a number of coils is advanced to the attachment site over the guide tether 236 and rotated around the guide rail 234 to sew the stent graft 220 to the attachment site. The guide rail 234 and guide tether 236 are connected to each other in such a way that the guide tether 236 can be removed after the stent graft 220 has been fixed to the attachment site, such as attachment with a fusible link, a clippable portion, or the like.

The graft material 224 can include more than one opening and associated guide rail in the side to accommodate flow to a number of branch vessels. For example, when the stent graft is deployed in the abdominal aorta, the graft material 224 can include one opening and guide rail associated with the right renal artery and another opening and guide rail associated with the left renal artery. The combination of openings and attachments can be selected as desired for a particular application, such as attachment in any combination of the distal end, the proximal end, and/or the side.

Figure 10:
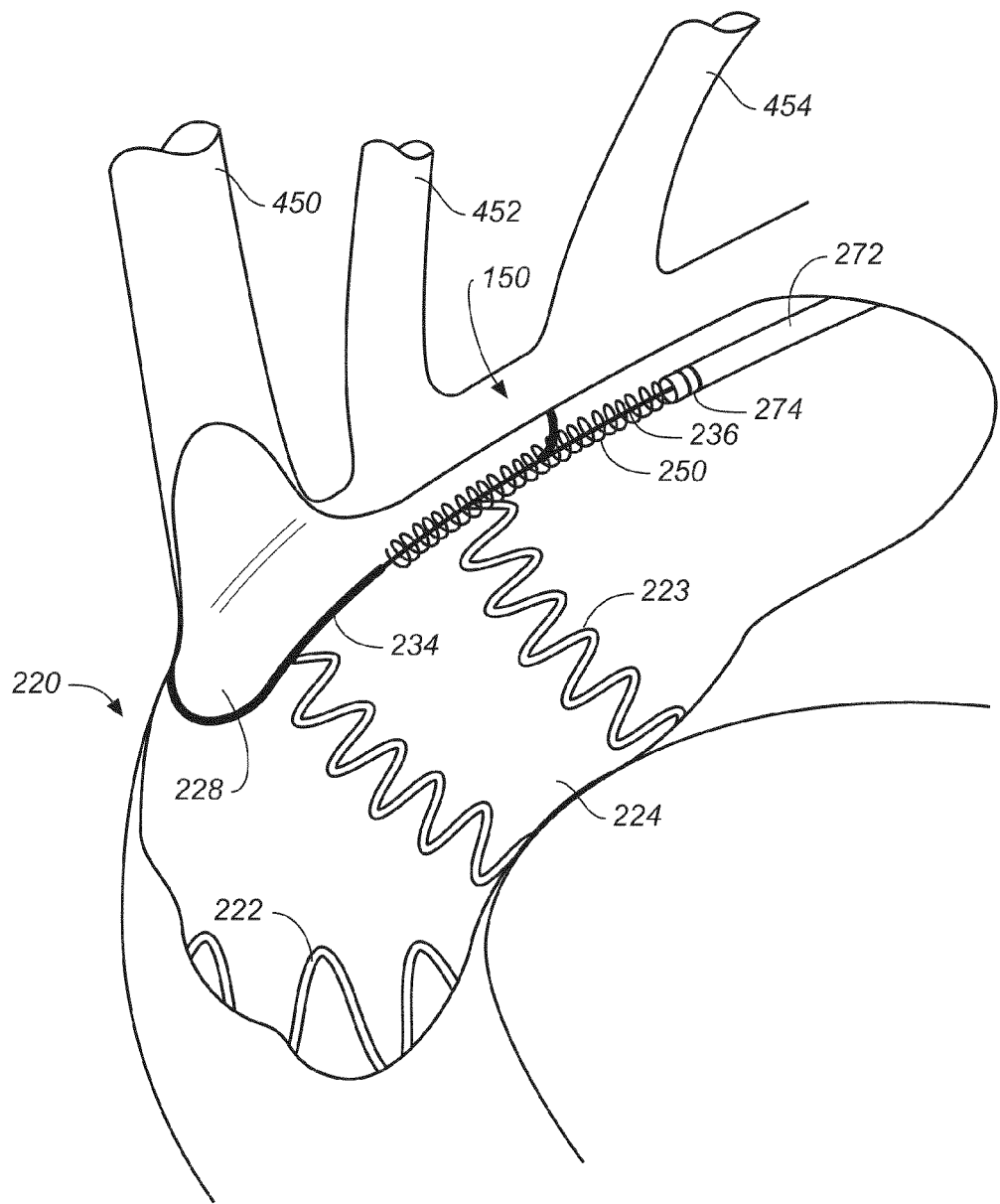
FIG. 10 is a cut away schematic view of deployment of the embodiment of a stent graft of FIG. 9.

FIG. 10 is a cut away schematic view of deployment of the embodiment of a stent graft of FIG. 9. In this example, the stent graft with an opening in the side of the graft material is being deployed in the aortic arch, with the helical anchor shown engaged part way around the guide rail. The attachment site is a circum-ostial ring encircling two ostia of branch vessels, such as the innominate, left common carotid, and/or left subclavian arteries. The helical anchor is sewing the side opening of the stent graft in place about the circum-ostial ring to seal the anchor connection between the stent graft and the vessel wall and provide blood flow to the branch vessels after the stent graft is deployed.

The driver 274 as it rotated is advanced by the pitch of the helical coils within and from the delivery catheter 272. The coils of the helical anchor 250 rotate about the guide tether 236 and the guide rail 234 to, advance the helical anchor 250 around the guide rail 234 and sew the stent graft 220 to the attachment site 150. In this example, the attachment site 150' is the circum-ostial ring about the ostia of the innominate artery 450 and left common carotid artery 452. The left sub-clavian artery 454 is outside the opening 228 in the graft material 224 after the stent graft 220 has been deployed.

In operation, the stent graft 220 is deployed in the vessel with the guide rail 234 aligned with the attachment site 150'. The driver 74 advances the helical anchor 250 along the guide tether 236 through the delivery catheter 272 and the stent graft lumen to the attachment site 150'. The helical anchor 250 engages the attachment site 150' through the stent graft 220 and is rotated to sew the stent graft 220 to the attachment site 150' along the guide rail 234. The guide rail support 223 and/or the guide rail 234 initially guide the helical anchor to engage the graft material and the vessel wall and then prevent the helical anchor 250 from plunging below the surface of the graft material and vessel wall, so that the helical anchor 250 engages the vessel wall approximately uniformly. Once the helical anchor 250 has sewn the desired length along the opening perimeter of the graft material 224, the guide tether 236 can be detached the from the guide rail 234 and the guide tether 236 withdrawn from the patient.

Figure 11A:
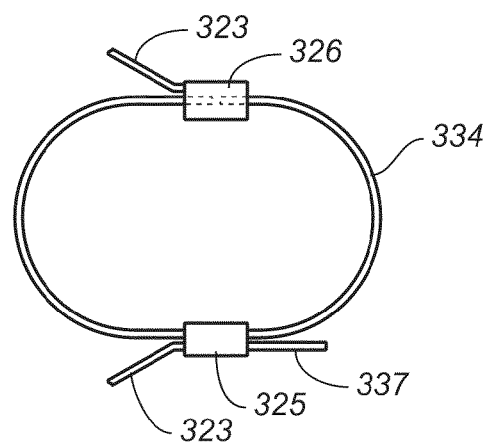
FIGS. 11A-11C are detail views of the tubular stent graft of FIGS. 9 & 10.
Figure 11B:
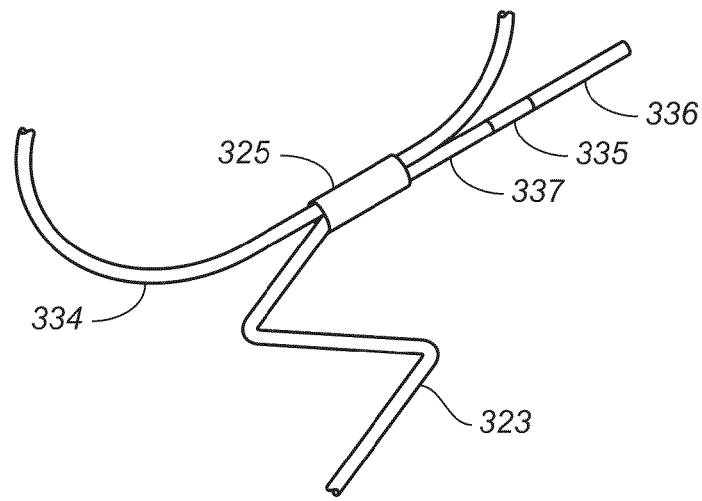
Figure 11C:
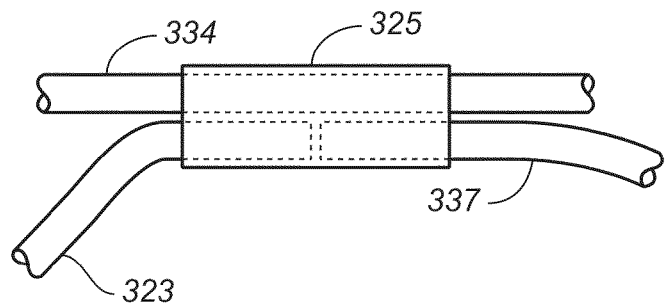

FIGS. 11A-11C are detail views of a tubular stent graft of FIGS. 9 & 10. In this example, the components are connected with crimped fittings. The guide rail 334 is a length of wire, with the ends of the wire held within crimped fitting 326 to form a loop. One end of guide rail support 323 is attached to the guide rail 334 with the crimped fitting 326 and the other end of the guide rail support 323 is attached to the guide rail 334 with the other crimped fitting 325. The crimped fitting 325 also connects solder spur 337 to the guide rail 334. The solder spur 337 is connected to the guide tether 336 with a fusible link 335. The guide tether 336 can be similar to a guidewire with a fine wire helically wrapped around the wire core.

The component design of FIGS. 11A-11C permits desired materials to be used for individual components. The solder spur 337 can be a material such as stainless steel which solders well to the fusible link 335, which can be a lead-free solder including silver and tin. The guide rail 334 and guide rail support 323 can be made of nitinol or another suitable nickel titanium alloy, and the crimped fittings 325, 326 can be nitinol, stainless steel, or the like.

Figure 12A:
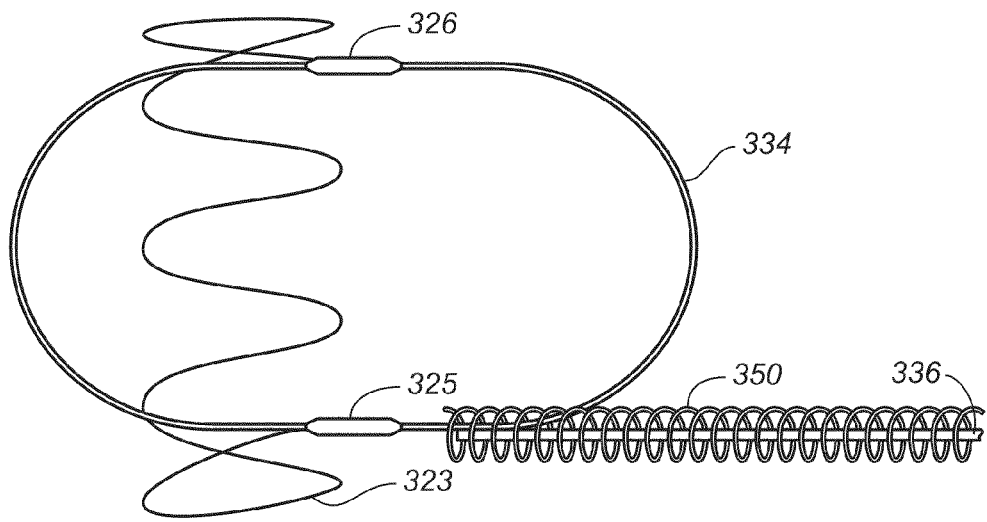
FIGS. 12A-12C are pictorial views of progressively sewing a helical anchor around a guide rail.
Figure 12B:
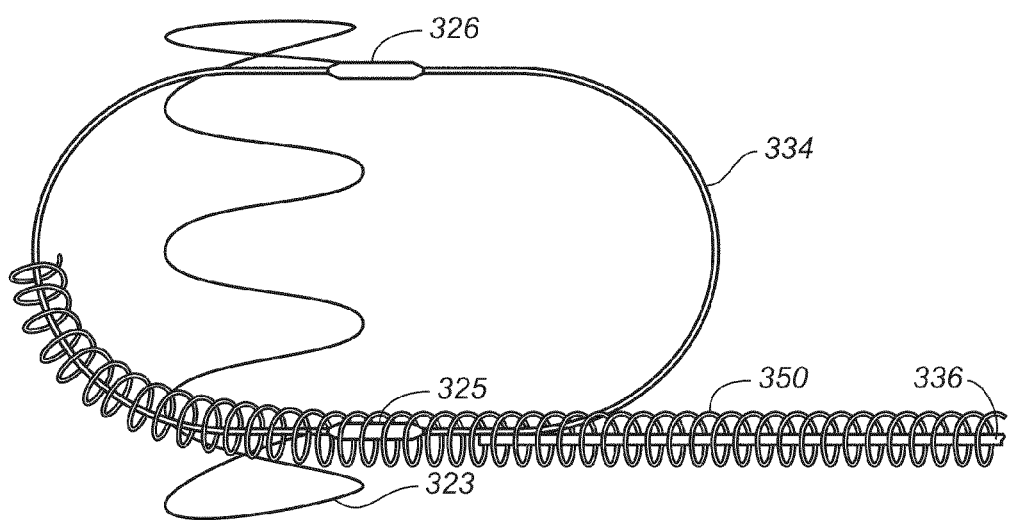
Figure 12C:
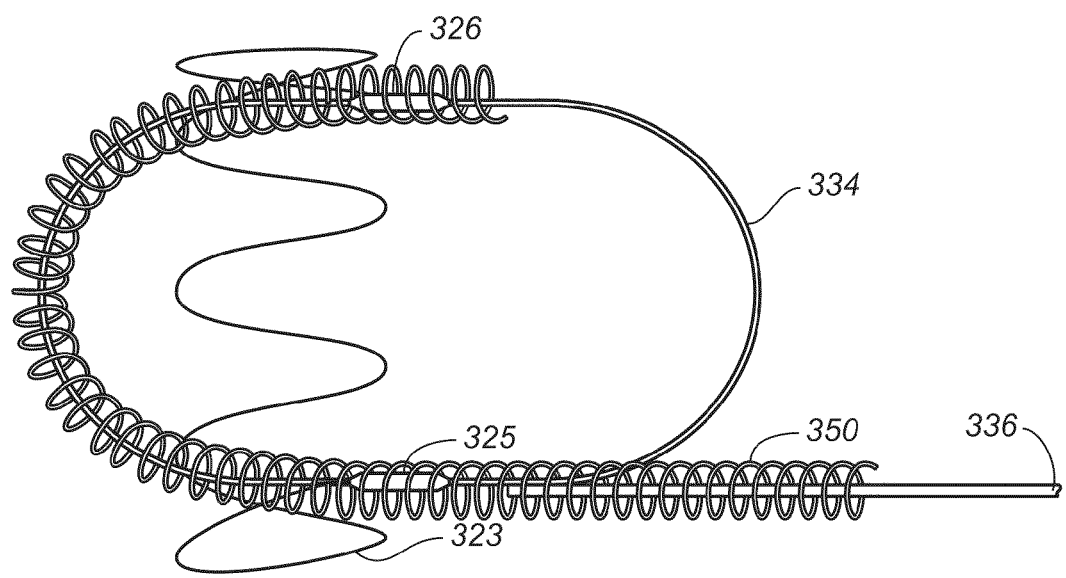

FIGS. 12A-12C are pictorial views of progressively sewing a helical anchor around a guide rail. The graft material has been omitted for clarity of illustration. Referring to FIG. 12A, the distal tip of the helical anchor 350 rotating about the guide tether 336 approaches the crimped fitting 325. Referring to FIG. 12B, the distal tip of the helical anchor 350 has passed over the crimped fitting 325 and beyond the first end of the guide rail support 323. Referring to FIG. 12C, the distal tip of the helical anchor 350 has passed over the crimped fitting 326 and beyond the second end of the guide rail support 323.

Figure 13:
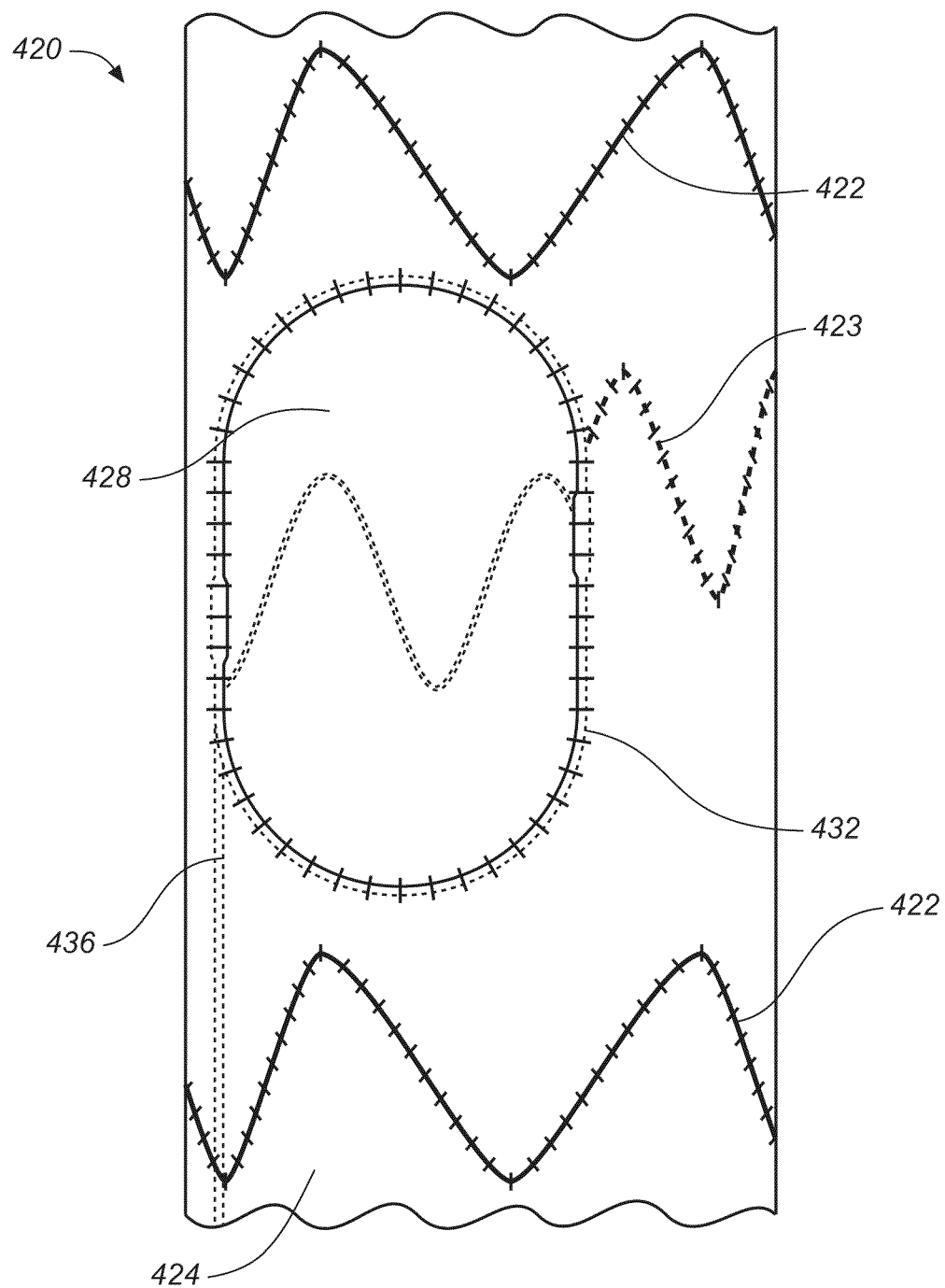
FIG. 13 is a pictorial view of another embodiment of a tubular stent graft.

FIG. 13 is a side view of another embodiment of a tubular stent graft. In this embodiment, the guide rail is sewn into the graft material to form the opening perimeter.

The stent graft 420 includes tubularly configured graft material 424 to which supports 422 are attached, with at least one opening 428 in the side of the tube. In this example, an opening 428 having an opening perimeter 432 is in the side of the graft material 424. The opening perimeter 432 is formed by stitching the graft material 424 around the guide rail to connect the graft material 424 to the guide rail. In this example, the guide rail supports 423 are sewn to the inside of the graft material 424 and the supports 422 are sewn to the outside of the graft material 424. The guide tether 436 is inside the graft material 424.

While specific embodiments according to the invention are disclosed herein, various changes and modifications can be made without departing from its spirit and scope.

The invention claimed is:

1. A stent graft for fixation at an attachment site comprising:
- graft material defining at least one opening having an opening perimeter;
- a support attached to the graft material;
- a guide rail attached around the opening perimeter;
- a helical anchor having a plurality of coils; and
- a guide tether attached to the guide rail;
- wherein the plurality of coils are rotatable around the guide rail to sew the stent graft to the attachment site, and wherein the guide tether is attached to the guide rail with a fusible link.

2. The stent graft of claim 1 wherein the at least one opening is in an end of the graft material.

3. The stent graft of claim 2 wherein the attachment site is a vessel wall circumference.

4. The stent graft of claim 1 wherein the at least one opening is in a side of the graft material.

5. The stent graft of claim 4 wherein the attachment site is a circum-ostial ring encircling at least one ostium.

6. The stent graft of claim 4 wherein the attachment site is a circum-ostial ring encircling a plurality of ostia.

7. The stent graft of claim 1 further comprising a guide rail support attached to the guide rail.

8. The stent graft of claim 1 wherein the graft material has a felt cuff around the opening perimeter, the plurality of coils being rotatable around the guide rail to sew the stent graft to the attachment site through the felt cuff.

9. A stent graft for fixation at an attachment site comprising:
- graft material defining at least one opening having an opening perimeter;
- a support attached to the graft material;
- a guide rail attached around the opening perimeter;
- a helical anchor having a plurality of coils; and
- a guide tether attached to the guide rail;
- wherein the plurality of coils are rotatable around the guide rail to sew the stent graft to the attachment site, and wherein a solder stub is crimped to the guide rail with a crimpable fitting, a fusible link is attached to the solder stub, and the guide tether is attached to the fusible link.

* * * * *